(12) United States Patent
Yang et al.

(10) Patent No.: US 11,448,583 B2
(45) Date of Patent: Sep. 20, 2022

(54) IMAGE ATLAS SYSTEMS AND METHODS

(71) Applicant: Beckman Coulter, Inc., Brea, CA (US)

(72) Inventors: Jun Yang, Agoura Hills, CA (US); Jon Tindel, Valley Village, CA (US)

(73) Assignee: Beckman Coulter, Inc., Brea, CA (US)

( * ) Notice: Subject to any disclaimer, the term of this patent is extended or adjusted under 35 U.S.C. 154(b) by 425 days.

(21) Appl. No.: 16/312,882

(22) PCT Filed: Jun. 23, 2017

(86) PCT No.: PCT/US2017/038953
§ 371 (c)(1),
(2) Date: Dec. 21, 2018

(87) PCT Pub. No.: WO2017/223412
PCT Pub. Date: Dec. 28, 2017

(65) Prior Publication Data
US 2019/0271632 A1  Sep. 5, 2019

Related U.S. Application Data

(60) Provisional application No. 62/354,520, filed on Jun. 24, 2016.

(51) Int. Cl.
*G01N 15/14* (2006.01)
*G01N 33/96* (2006.01)
(Continued)

(52) U.S. Cl.
CPC ..... *G01N 15/1404* (2013.01); *G01N 15/1434* (2013.01); *G01N 15/1463* (2013.01);
(Continued)

(58) Field of Classification Search
CPC ........... G01N 15/1404; G01N 15/1434; G01N 15/1463; G01N 15/1475; G01N 33/5094;
(Continued)

(56) References Cited

U.S. PATENT DOCUMENTS

2010/0070904 A1  3/2010  Zigon
2010/0169811 A1  7/2010  Yamada
(Continued)

FOREIGN PATENT DOCUMENTS

BR  112018076406 A2  4/2019
CN  101211356 A  7/2008
(Continued)

OTHER PUBLICATIONS

PCT/US2017/038953 received an International Preliminary Report on Patentability, dated Jan. 3, 2019, 8 pages.
(Continued)

*Primary Examiner* — Brian J. Sines
(74) *Attorney, Agent, or Firm* — Schwegman Lundberg & Woessner, P.A.

(57) ABSTRACT

In some embodiments, a process and system are provided for generating a user interface for classification of a sample image of a cell that includes receiving a sample image of a sample particle from a biological sample and selecting reference images that each portray a reference particle of a biological sample. The reference images can be ordered based on similarity and the reference images can be selected based on the order. The first selected reference image can be aligned with the sample image and expanded such that the adjacent edges of the reference image and sample image are the same. The expanded image can be dynamically filled. The sample image and the expanded reference image can be displayed in a user interface.

6 Claims, 18 Drawing Sheets

(51) Int. Cl.

| | |
|---|---|
| *G01N 33/50* | (2006.01) |
| *G06T 5/00* | (2006.01) |
| *G06F 3/048* | (2013.01) |
| *G06T 7/00* | (2017.01) |
| *G06T 11/00* | (2006.01) |
| *G06K 9/62* | (2022.01) |
| *G06F 16/50* | (2019.01) |
| *G06V 10/44* | (2022.01) |
| *G06V 20/69* | (2022.01) |
| *G01N 15/10* | (2006.01) |

(52) U.S. Cl.
CPC ..... *G01N 15/1475* (2013.01); *G01N 33/5094* (2013.01); *G01N 33/96* (2013.01); *G06F 3/048* (2013.01); *G06F 16/50* (2019.01); *G06K 9/6201* (2013.01); *G06K 9/6253* (2013.01); *G06T 5/005* (2013.01); *G06T 7/001* (2013.01); *G06T 11/001* (2013.01); *G06V 10/44* (2022.01); *G06V 20/698* (2022.01); *G01N 2015/1006* (2013.01); *G06T 2207/30024* (2013.01)

(58) Field of Classification Search
CPC ........ G01N 33/96; G01N 15/14; G01N 33/50; G06F 16/50; G06F 3/048; G06K 9/00147; G06K 9/4604; G06K 9/6201; G06K 9/6253; G06T 5/005; G06T 7/00; G06T 7/0012; G06T 7/0014; G06T 7/001
See application file for complete search history.

(56) References Cited

U.S. PATENT DOCUMENTS

| | | |
|---|---|---|
| 2014/0273067 A1 | 9/2014 | Wanders |
| 2015/0169992 A1* | 6/2015 | Ioffe ........................ G06K 9/46 382/218 |
| 2016/0026852 A1* | 1/2016 | Zahniser ............ G01N 15/1475 382/134 |
| 2016/0041083 A1 | 2/2016 | Wanders et al. |
| 2017/0046550 A1* | 2/2017 | Lee ........................ G06K 9/001 |

FOREIGN PATENT DOCUMENTS

| | | |
|---|---|---|
| CN | 101339556 A | 1/2009 |
| CN | 101539930 A | 9/2009 |
| CN | 102279864 A | 12/2011 |
| CN | 102467564 A | 5/2012 |
| CN | 102598054 A | 7/2012 |
| CN | 102621053 A | 8/2012 |
| CN | 104809245 A | 7/2015 |
| CN | 105121620 A | 12/2015 |
| CN | 105631872 A | 6/2016 |
| EP | 0 660 103 A2 | 6/1995 |
| EP | 0660103 A3 | 3/1996 |
| EP | 3475683 A1 | 5/2019 |
| JP | H055733 A | 1/1993 |
| JP | H08315105 A | 11/1996 |
| JP | 2008131542 A | 6/2008 |
| JP | 2008188177 A | 8/2008 |
| JP | 2016012346 A | 1/2016 |
| JP | 2016517515 A | 6/2016 |
| JP | 2019527876 A | 10/2019 |
| WO | 2004/046834 A1 | 6/2004 |
| WO | WO-2013001678 A1 | 1/2013 |
| WO | 2014/164757 A1 | 10/2014 |
| WO | WO-2015035477 A1 | 3/2015 |
| WO | WO-2014164757 A8 | 9/2015 |
| WO | 2016/025236 A1 | 2/2016 |
| WO | WO-2017223412 A1 | 12/2017 |

OTHER PUBLICATIONS

Kasdan H. L. et al.: "Comparison of 1-24 pathological cast analytical performance and flagging of automated urine sediment analyzers: A new flow imaging system versus flow cytometry", Clinical Chemistry, American Association for Clinical Chemistry, Washington, DC, vol. 49, Issue 6, Jun. 1, 2003 (Jun. 1, 2003), page AI60, XP009195506, ISSN: 0009-9147, Abstract.
Kasdan H. L. et al.: "Comparison of automated urine sediment analysis methods: A new flow imaging system versus flow cytometry", Clinical Chemistry, American Association for Clinical Chemistry, Washington, DC, vol. 48, No. 6 Suppl, Jun. 1, 2002 (Jun. 1, 2002), page A5, XP009195507, ISSN: 0009-9147, Abstract.
PCT/US2017/038953 filed Jun. 23, 2017, received an International Search Report and Written Opinion, dated Nov. 14, 2017, 250.
"Brazilian Application Serial No. 1120180764060, Voluntary Amendment filed Jun. 19, 2020", w/ English claims, 63 pgs.
"Chinese Application Serial No. 201780039295.5, Office Action dated Jan. 11, 2021", w/ English translation, 24 pgs.
"European Application Serial No. 17736838.8, Response filed Jul. 31, 2019 to Communication Pursuant to Rules 161 and 162 dated Jan. 31, 2019", 18 pgs.
"Korean Application Serial No. 10-2019-7000075, Voluntary Amendment filed Jun. 15, 2020", w/ English claims, 14 pgs.
"Chinese Application Serial No. 201780039295.5, Office Action dated Jun. 18, 2021", w/ English translation, 20 pgs.
"Chinese Application Serial No. 201780039295.5, Response filed May 13, 2021 to Office Action dated Jan. 11, 2021", w/ English claims, 24 pgs.
"Indian Application Serial No. 201847046568, First Examination Report dated Jun. 29, 2021", 6 pgs.
"Japanese Application Serial No. 2018-566963, Notification of Reasons for Refusal dated Mar. 5, 2021", w/ English Translation, 5 pgs.
"Japanese Application Serial No. 2018-566963, Response filed Jun. 2, 2021 to Notification of Reasons for Refusal dated Mar. 5, 2021", w/ English claims, 17 pgs.
"Chinese Application Serial No. 201780039295.5, Response Filed Nov. 2, 2021 to Office Action dated Jun. 18, 2021", with English claims, 25 pages.
"Chinese Application Serial No. 201780039295.5, Decision of Rejection dated Mar. 3, 2022", with English translation, 14 pages.
"Chinese Application Serial No. 201780039295.5, Response Filed Nov. 2, 2021 to Office Action dated Jun. 18, 2021", W/ English Claims, 25 pgs.
"Brazilian Application Serial No. 1120180764060, Office Action dated Jun. 15, 2022", w/English translation, 4 pgs.

* cited by examiner

400 ⬊

```
┌─────────────────────────────────────────────────────────────┐
│ Compare the sample image with each reference image of the   │
│ plurality of reference images                               │
│                                                         405 │
└─────────────────────────────────────────────────────────────┘
```
```
┌─────────────────────────────────────────────────────────────┐
│ Determine the similarity of each reference image to the     │
│ sample image                                                │
│                                                         410 │
└─────────────────────────────────────────────────────────────┘
```

```
┌─────────────────────────────────────────────────────────────┐
│ Generate a feature vector for each of the reference images  │
│ of the plurality of reference images and the sample image   │
│                                                         505 │
└─────────────────────────────────────────────────────────────┘
```
```
┌─────────────────────────────────────────────────────────────┐
│ Calculate a distance metric for each reference image of the │
│ plurality of reference images from the sample image based   │
│ on the generated feature vectors                            │
│                                                         510 │
└─────────────────────────────────────────────────────────────┘
```

Determine a first display location for displaying the sample image in the user interface within a first cell of a grid  605

Determine a second display location adjacent to the first display location for displaying the first reference image in the user interface within a second cell of the grid  610

Align a centroid of the first reference image within the second display location with a centroid of the sample image within the first display location  615

Expand the background of the first reference image within the second cell to fill the second cell  705

Determine a background color of the first reference image  710

Fill the expanded background of the first reference image with the background color  715

FIG. 7

IMAGE ATLAS SYSTEMS AND METHODS

CROSS-REFERENCE TO RELATED APPLICATIONS

This application is a U.S. national phase under 35 U.S.C. § 371 of PCT International Application Number PCT/US2017/038953, filed on Jun. 23, 2017, entitled "IMAGE ATLAS SYSTEMS AND METHODS," which claims the benefit of priority to U.S. Provisional Patent Application No. 62/354,520, filed on Jun. 24, 2016, entitled "IMAGE ATLAS SYSTEMS AND METHODS," each of which are hereby incorporated by reference in their entireties for all purposes.

TECHNICAL FIELD

The present disclosure relates generally to analysis of images for clinical use. More specifically, but not by way of limitation, the present disclosure relates to analysis of images of cells and particles gathered for clinical diagnostics such as hematology and urinalysis and normalization of display of the images to allow a user to perform clinical analysis without distraction based on irrelevant discrepancies between the images.

BRIEF DESCRIPTION OF THE DRAWINGS

A further understanding of the nature and advantages of various examples may be realized by reference to the following figures.

FIG. 4 illustrates a flowchart of an example of a process for determining an order of images based on similarity according to an embodiment.

FIG. 5 illustrates a flowchart of an example of a process for determining a similarity between images according to an embodiment.

FIG. 6 illustrates a flowchart of an example of a process for aligning images according to an embodiment.

FIG. 7 illustrates a flowchart of an example of a process for dynamically filling the background of an image according to an embodiment.

DETAILED DESCRIPTION

Figure 1:
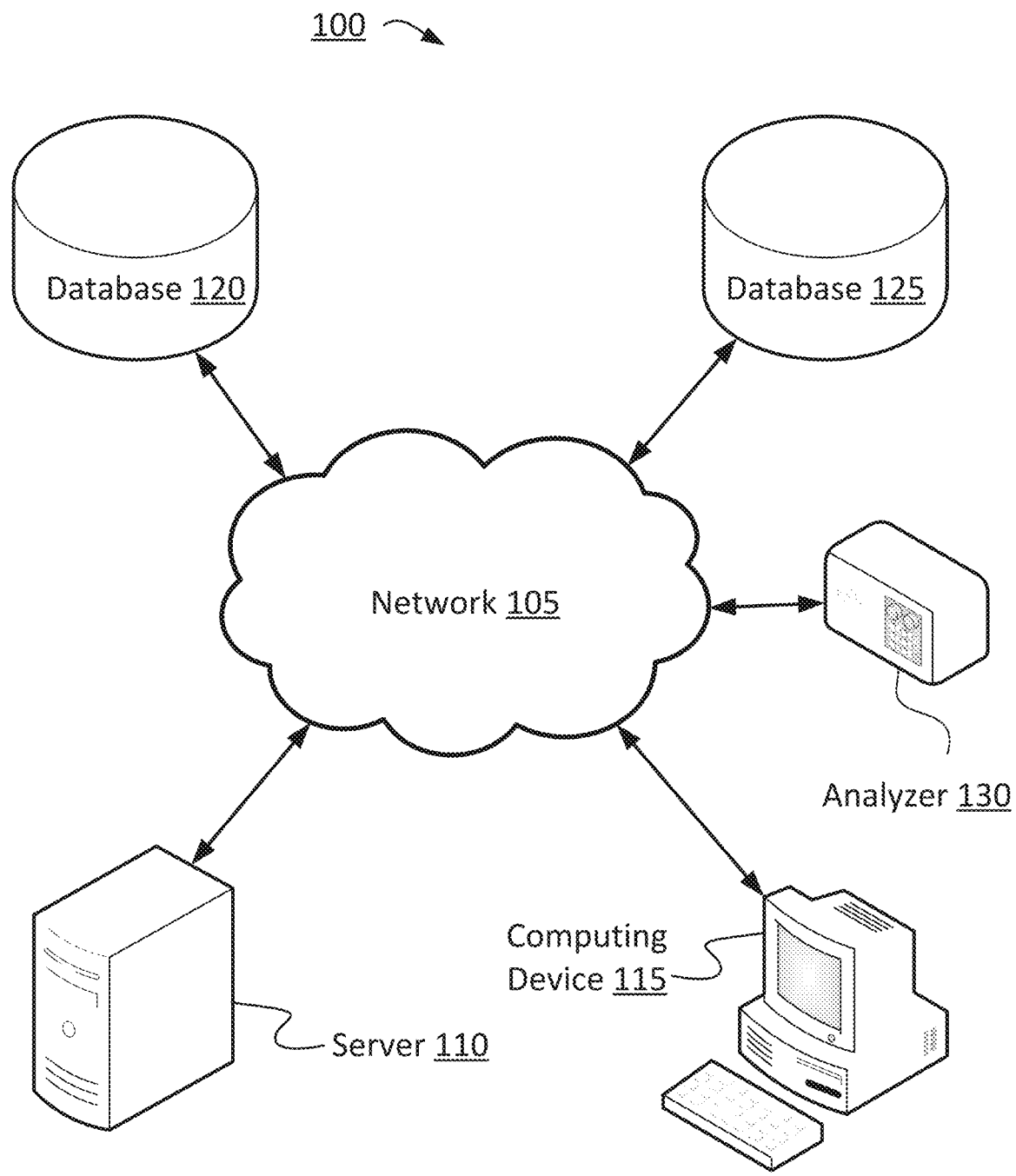
FIG. 1 illustrates a block diagram of an example system usable for performing image analysis, normalization, and display according to an embodiment.

Analysis of a cell or particle from a living organism (e.g., humans, animals, and plants) can be used as a medical diagnostic tool used to identify diseases and cell defects as well as healthy cells. Capturing the cells or particles for analysis can be done by collection of particles through, for example, fluids from the living organism (i.e., a biological sample). For example, a blood sample from a person contains cells that can be analyzed to determine if the cells are healthy or have some problem that can be diagnosed. For example, blood samples from patients who come under the care of a physician can be evaluated using a hematology system that is equipped to obtain multiple light angle detection parameters, such as the system described in patent application Ser. No. 14/775,448 entitled HEMATOLOGY SYSTEMS AND METHODS, filed Sep. 11, 2015, and published as US 2016-0041083 A1 on Feb. 11, 2016. As another example, urine samples can be evaluated. To analyze the cells or particles, it can be beneficial to image the cells and perform a comparison of the cells against other images of cells with known characteristics. While some analysis and comparisons can be done through an automated system, not all images of cells are sufficiently clear, have a known issue, or are similar enough to images of cells with known issues for automation to work properly or effectively. In that case, manual comparison by medical diagnostic personnel can be performed. Optionally, a user interface can be provided that provides images of sample cells to be diagnosed or categorized and reference images of cells with known characteristics. The sample image for categorization can have differences from the reference image that can distract from the comparison, even though the cells in the reference image and the sample image might have the same features or characteristics or be the same type of cell. Differences such as image size, orientation, and gaps between the displayed images are all examples of differences that can distract from the comparison of the cell images. Embodiments described herein can compensate for those distractions and provide an optimized user interface for comparing the sample and reference images using an image atlas.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape, and any size. Particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes, and blasts. In addition to mature RBCs, members of RBCs may include nucleated RBCs (NTRCs) and reticulocytes. PLTs may include "giant" PLTs and PLT clumps. Platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles. Throughout the specification, the images are described as being an image of a cell or a particle. Though referred to as a cell in many cases, the images can be of any particle. "Image" means the visual impression of something produced by an optical device, such as a lens, mirror, camera, or microscope.

Exemplary urine particles can include urine sediment particles. Exemplary urine sediment particles can include erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments. Exemplary cells can include red blood cells, white blood cells, and epithelials. Exemplary casts can include acellular pigment casts, unclassified cast (e.g. granular casts). Exemplary acellular casts can include, for example, waxy casts, broad casts, fatty casts, and crystal casts. Exemplary cellular casts can include, for example, RBC casts, WBC casts, and cellular casts. Exemplary crystals can include, for example, calcium oxalate, triple phosphate, calcium phosphate, uric acid, calcium carbonate, leucine, cystine, tyrosine, and amorphous crystals. Exemplary non-squamous epithelial cells can include, for example, renal epithelials and transitional epithelials. Exemplary yeast can include, for example, budding yeast and yeast with pseudohyphae. Exemplary urinary sediment particle can also include RBC clumps, fat, oval fat bodies, and trichomonas. The described systems and methods may be useful, for example, in characterizing particles in biological fluids, such as detecting and quantifying erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments, categorization and subcategorization, counting and analysis.

In the following description, for the purposes of explanation, specific details are set forth in order to provide a thorough understanding of embodiments of the invention. However, it will be apparent that various embodiments may be practiced without these specific details. The figures and description are not intended to be restrictive.

Systems depicted in some of the figures may be provided in various configurations. Optionally, the systems may be configured as a distributed system where one or more components of the system are distributed across one or more networks in a cloud computing system. All features of the described systems are applicable to the described methods mutatis mutandis, and vice versa.

FIG. 1 illustrates a block diagram of an example system 100 usable for performing image analysis, normalization, and display. The system 100 can include a network 105 through which various components can communicate, including database 120, database 125, server 110, computing device 115, and analyzer 130.

Analyzer 130 can collect images of living organism particles and cells through, for example, a bodily fluid system that captures images of bodily fluid cells as described in detail in patent application Ser. No. 14/775,448 entitled HEMATOLOGY SYSTEMS AND METHODS, filed Sep. 11, 2015. Analyzer 130 can collect images and store them in database 120 as sample cell images. Reference images can be collected through analyzer 130 and/or through other capture methods for comparison and stored in database 125.

Database 120 can store sample images for analysis. Database 125 can store an image atlas (i.e., database of reference images) for comparison during analysis of the sample images stored in database 120. Optionally, database 120 and database 125 can be a single database (e.g., with the sample images stored in a different table than the reference images). Databases 120 and 125 can be any suitable database including, for example, a Microsoft® SQL Server® database, an Oracle® database, or a Microsoft® Excel® spreadsheet.

Network 105 can be any suitable number or type of networks or links, including, but not limited to, a dial-up network, a local area network (LAN), wide area network (WAN), public switched telephone network (PSTN), a cellular network, a WiFi network, the Internet, an intranet or any combination of hard-wired and/or wireless communication links. The network 105 can include one or more sub-networks. In some examples, two or more components of the system (e.g., the computing device 115, server 110, databases 120 and 125, analyzer 130, or any combination of these) can be connected to, and communicate via, the network 105.

Figure 2:
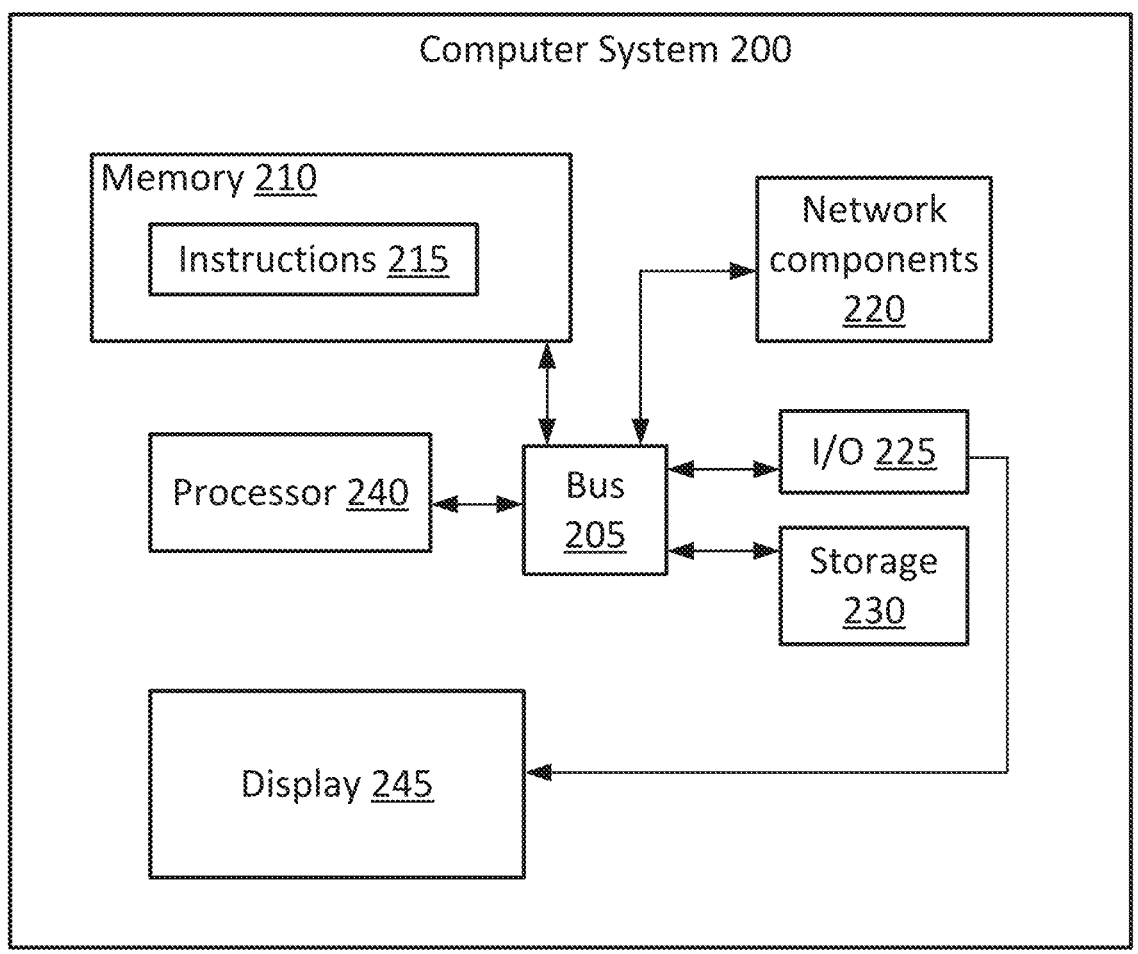
FIG. 2 illustrates a block diagram of an example computer system usable for performing image analysis, normalization, and display according to an embodiment.

Computing device 115 can be a computing system 200 as described with respect to FIG. 2. The computing device 115 can be a system that is capable of performing image analysis, normalization, and display as discussed in more detail herein. The computing device 115 can be a system utilized by a user and, while depicted as a desktop computer can be any user device including a laptop or a wireless device (e.g., smartphone, tablet, Personal Data Assistant (PDA), e-reader, or smart watch).

Optionally, server 110 can be a computing system 200 as described with respect to FIG. 2. The server 110 can be capable of performing image analysis and normalization and, because a server sometimes does not include its own display device, send the resulting images to the computing device 115 for display in a user interface, for example. Optionally, the server 110 can be any suitable type of server. The server can be, for example, in a server farm or a rack server. Computing device 115 and server 110 can be in a cloud computing environment, for example.

FIG. 2 illustrates a block diagram of an example computer system 200 usable for performing image analysis, normalization, and display. The computing device 200 can be or include, for example, a laptop computer, desktop computer, tablet, e-reader, smart phone or mobile device, smart watch, personal data assistant (PDA), or other electronic device. Computing device 200 can be, for example, computing device 115 or server 110.

The computing device 200 can include a processor 240 interfaced with other hardware via a bus 205. A memory 210, which can include any suitable tangible (and non-transitory) computer readable medium, such as RAM, ROM, EEPROM, or the like, can embody program components (e.g., instructions 215) that configure operation of the computing device 200. In some examples, the computing device 200 can include input/output ("I/O") interface components 225 (e.g., for interfacing with a display 245, keyboard, or mouse) and additional storage 230.

The computing device 200 can include network components 220. Network components 220 can represent one or more of any components that facilitate a network connection. In some examples, the network components 220 can facilitate a wireless connection and include wireless interfaces such as IEEE 802.11, Bluetooth, or radio interfaces for accessing cellular telephone networks (e.g., a transceiver/antenna for accessing CDMA, GSM, UMTS, or other mobile communications network). In other examples, the network components 220 can be wired and can include interfaces such as Ethernet, USB, or IEEE 1394.

Although FIG. 2 depicts a single computing device 200 with a single processor 240, the system can include any number of computing devices 200 and any number of processors 240. For example, multiple computing devices 200 or multiple processors 240 can be distributed over a wired or wireless network (e.g., a Wide Area Network, Local Area Network, or the Internet), for example network 105.

The multiple computing devices 200 or multiple processors 240 can perform any of the steps of the present disclosure individually or in coordination with one another. For example, the processor 240 and/or the computing device 200 can be, for example, the computing device 115 and/or server 110 of FIG. 1.

Figure 3:
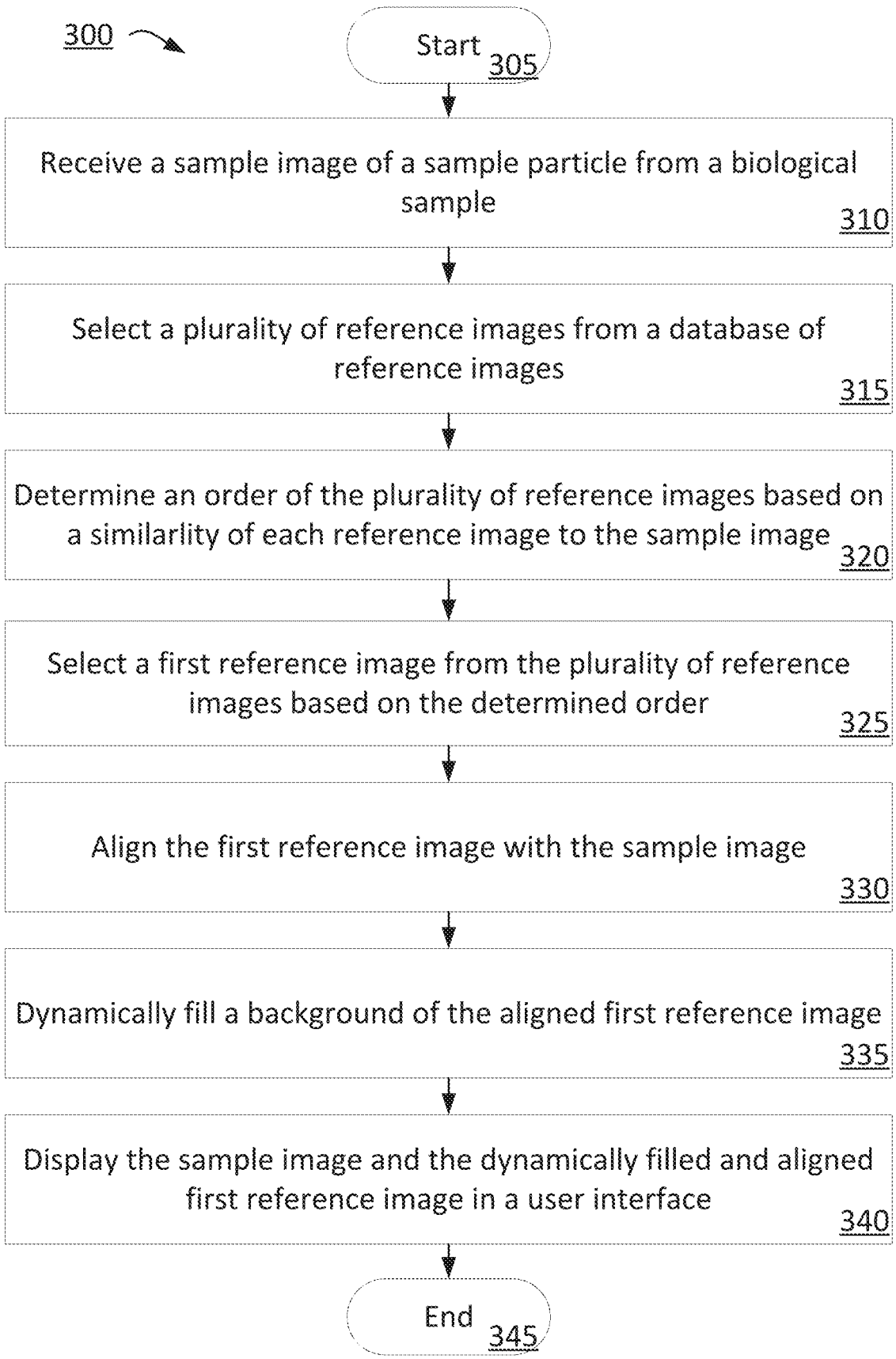
FIG. 3 illustrates a flow chart of an example of a process for performing image analysis, normalization, and display according to an embodiment.

FIG. 3 illustrates a flow chart of an example of a process 300 for performing image analysis, normalization, and display. This process 300 can be implemented on, for example the system 100 of FIG. 1 and more specifically as program code on computer system 200 of FIG. 2.

The process 300 begins at 305 on, for example, computer system 200 of FIG. 2. At 310 the computer system 200 can receive a sample image of a sample particle (e.g., cell) from a living organism. As discussed briefly above, cells and particles of a living organism can be imaged or photographed using an imaging system (e.g., analyzer 130) that uses a collected biological sample (e.g., a urine or blood sample) from the organism. The images can be magnified before or after capture and depict an image of a single cell or particle, such as sample image 905 of FIG. 9. The sample image can be received through network 105 of FIG. 1 from, for example, database 120 of FIG. 1, at the computing device 115 (shown in more detail as computer system 200 of FIG. 2).

At 315 the computer system 200 can select a plurality of reference images from a database of reference images. The database of reference images can be, for example, database 125 of FIG. 1. The database can contain any number of reference images. The reference images can be populated through a similar capture method as described above with respect to the sample image. A reference image can be, for example, reference image 910 of FIG. 9. The reference images can be populated through a user selected library of reference images that are stored in database 125. Optionally, the user selected images can be from a previously captured library of reference images. Optionally, the user selected images can include images that were sample images that the user adds to the reference images database. Optionally, the user selected images can use randomly generated Globally Unique Identifier (GUID) based filenames to ensure uniqueness and portability among systems. Reference images can be stored in any suitable format (e.g., *.png, *.gif, *.jpg). Reference images can be stored as captured, meaning the images may be of differing file sizes, pixel heights, pixel widths, and/or magnification of the imaged cell, for example.

The reference images can be of cells or particles that contain known features or are certain types of known cells or particles. For example, a whole blood sample normally comprises three major classes of blood cells including red blood cells (erythrocytes), white blood cells (leukocytes), and platelets (thrombocytes). Each class can be further divided into subclasses of members. For example, five major types of subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity, and other causes. Red blood cell subclasses may include reticulocytes and nucleated red blood cells. As another example, the imaged cell can be a sickle cell. The reference images can include annotations that can identify the category of the cell within the reference image or tags that identify features or characteristics of the cell within the reference image. As an example, an annotation on an image of a cell known to be a sickle cell can identify the cell as a sickle cell. As another example, an annotation on an image of a cell known to be a red blood cell can identify the cell as a red blood cell. Some reference images can include multiple tags that identify multiple features or characteristics of a cell. For example, the cell can be annotated as a red blood cell and have an additional tag that identifies the cell as a reticulocyte. The cells or particles can be tagged as, for example, a neutrophil, lymphocyte, monocyte, eosinophil, basophil, platelet, reticulocyte, nucleated red blood cell (RBC), blast, promyelocyte, myelocyte, metamyelocyte, red blood cell (RBC), cell, bacteria, particulate matter, cell clump, or cellular fragment or component.

Optionally, computer system 200 can select multiple reference images from the database of reference images by selecting, for example, all reference images having a specific tag and/or annotation. As an example, the computer system 200 can select all reference images from the database that are annotated as a red blood cell. As another example, the computer system 200 can select all reference images from the database having a white blood cell annotation. Optionally, the computer system 200 can allow a user to select the tag or annotation used for selecting the reference images. Optionally, computer system 200 can select all reference images in the reference image database. Optionally, computer system 200 can allow a user to select desired reference images from the reference image database. Optionally, the computer system 200 can allow the user to select additional tags as filters and, for example, select all images classified as white blood cells and further tagged as a neutrophil.

Tagging or annotation onto images can provide an effective method for fast image retrieval. For a large number of reference images with potentially many different subtypes, based on variations either in physical characteristics, or in disease stages for the same class type (classification), it can be beneficial to provide a subset targeting one or more subtypes. This can be done via hierarchical tagging, such as tagging within an annotation that identifies a class of the imaged cell. For example, a reference image can include an annotation that the cell is a red blood cell ("RBC") (i.e., annotation of RBC, that the imaged cell is in the RBC class) and a tag marking the reference image as having a specific characteristic as well as the RBC annotation, for example a nucleated red blood cell can have a tag identifying it as nucleated.

At 320, computer system 200 can determine an order of the plurality of reference images based on a similarity of each reference image to the sample image. It can save a great deal of time to order the reference images such that the most similar are displayed first. As discussed previously, the sample image can be displayed along with the reference images in a user interface for comparison to identify characteristics, features, or the type of cell imaged in the sample image. Displaying the most similar images first can limit the amount of time it takes to find a reference image that matches the sample image for classifying the sample image as the same type of cell in the reference image or for identifying that the sample image has the same characteristic or feature as the reference image. Computer system 200 can determine the order by, for example, comparing the sample image with each of the selected reference images as described in more detail with respect to FIGS. 4 and 5.

At 325, computer system 200 can select a first reference image from the plurality of reference images based on the determined order. After the computer system 200 has determined the order of the reference images such that the first reference image is the one that was determined to be most similar, the second reference image is the one that was determined to be the second most similar, and so forth, the computer system 200 can select the first reference image for performing the analysis, normalization, and display. After performing the remaining steps of process 300 on the first reference image, computer system 200 can select the second reference image for performing the analysis, normalization, and display in the remaining steps of process 300 and continue repeating the steps on each reference image of the plurality of reference images until all of the selected reference images have been analyzed, normalized, and displayed according to process 300.

At 330, computer system 200 can align the first reference image with the sample image. Alignment of the first reference image with the sample image can be, for example, for display of the images to the user through the user interface. The alignment can include aligning the adjacent edge of the images as well as centering the images with respect to each other for display in a user interface. An example of a type of alignment that can be performed is described in more detail with respect to FIG. 6. Optionally, the adjacent edges of the sample image and the reference image are not the same size. In such cases, the smaller image can be expanded to match the size of the larger image. For example, optionally, the smaller image can be zoomed to expand to the same size as the larger image. Optionally, the image can be superimposed over an image patch that has the same size adjacent edge as the larger image. Optionally, each image can be placed for display in a cell of a grid, and the cell of the grid can have a matching background color that appears in a display to resize the smaller image to the size of the larger image.

Optionally, the number of reference images for display in a user interface can be between 1 and 8. The alignment and expansion can be done for any number of reference images, and the reference images can be aligned and expanded in order based on the image that shares an adjacent edge. See the description with respect to FIG. 11 for more detail on optional image display layout. In mathematical terms, assuming that $I_{i,j}$ is the reference image at the i-th row, j-th column in a grid of m×n with i∈[0, m−1], j∈[0, n−1], having width of $W_{i,j}$ and height of $H_{i,j}$. The alignment and expansion can be done by calculating the i-th row height $RH_i$ and j-th column width $CW_j$ for the display grid as follows:

$$RH_i = \underset{j=0}{\overset{n-1}{\text{MAX}}}(H_{i,j})$$

$$CW_j = \underset{i=0}{\overset{m-1}{\text{MAX}}}(W_{i,j})$$

Depending on the relative sizes of the sample image and the list of reference images for display, the final row height or column width for particular row/column in the display grid can cause either the sample image or the reference image to require expansion. Optionally the image background filling can apply to any image which has a different size from the calculated grid cell's width or height. And the image itself can be positioned at the center of the associated grid cell without scaling or resizing to preserve 100% fidelity to the original image.

At 335, computer system 200 can dynamically fill the background of the aligned first reference image. During the alignment step, the background of the first reference image can be expanded to ensure that the displayed image has a same size adjacent edge to the sample image. The expanded background can be dynamically filled with substantially the same color as the existing background of the reference image to ensure uniformity and remove the distraction of having gaps between the images containing different background colors. Colors for any image can include red, green, blue, and alpha channels, for example. The background can be filled by determining a color that matches the reference image background and filling in the expanded background with the determined color, as described in more detail with respect to FIG. 7. Optionally, the background is filled by superimposing the reference image over a patch filled in with the determined background color. During display, the patch can be, for example, a cell of a grid of cells. It is noted at this time that two different types of cells are discussed in this application. The images of cells (i.e., reference images or sample images) are images of body cells of a living organism. A cell of a grid is a different type of cell, like a cell in a table. Throughout the application, when talking about a cell, a body cell that has been imaged is intended unless specifically noted a cell of a grid is being discussed.

Optionally, the alignment of the sample image and the reference image can result in the sample image being resized to expand the background (e.g., because the sample image is smaller than the reference image). In such cases, the background of the sample image can be dynamically filled in the same manner as described above with respect to dynamically filling the background of the first reference image.

At 340, computer system 200 can display the sample image and the dynamically filled and aligned first reference image in a user interface. Examples of user interface displays of a sample image and one or more reference images are shown at FIGS. 9-18. Optionally, the user interface can be displayed in the display device associated with computer system 200. For example, computing device 115, which can be any user device with a monitor that can display the user interface including a desktop, laptop, smartphone, tablet, or any other suitable computing device 115 including a display monitor, can be computer system 200. Optionally, computer system 200 can be server 110. In such embodiments, server 110 may not include a specific display monitor so server 110 can send the information (e.g., reference images and sample image and associated calculated layout and color information) for display to computing device 115 for display to a user in a user interface.

Process 300 can end at 345. As discussed above, optionally, steps 325, 330, and 335 can be performed on the first reference image and repeated for each reference image until each of the selected reference images have been aligned and dynamically filled. Optionally in which the reference images are each aligned and dynamically filled in, the display step can be performed for each reference image individually, for all selected reference images at the same time (only once after all selected reference images have been aligned and dynamically filled), or in groups of a certain number of reference images at a time (e.g., 8 reference images are displayed at a time with the sample image such as in FIG. 12).

FIG. 4 illustrates a flowchart of an example of a process 400 for determining an order of images based on similarity. Process 400 can be performed as part of step 320 of FIG. 3. Process 400 can be implemented on, for example the system 100 of FIG. 1 and more specifically as program code on computer system 200 of FIG. 2.

At 405, computer system 200 can compare the sample image with each reference image of the plurality of reference images. The comparison can be done, for example, by generating a feature vector for each reference and sample image and calculating a distance metric between each reference image and the sample image, as described in more detail with respect to FIG. 5.

At 410, computer system 200 can determine the similarity of each reference image to the sample image. This determination can be done based on, for example, the calculated distance metric discussed with respect to FIG. 5.

FIG. 5 illustrates a flowchart of an example of a process 500 for determining a similarity between images. Process 500 can be performed as part of step 405 of FIG. 4. Process 500 can be implemented on, for example the system 100 of FIG. 1 and more specifically as program code on computer system 200 of FIG. 2.

At 505, computer system 200 can generate a feature vector for each of the reference images of the plurality of reference images and the sample image. The feature vector can include information on multiple features of each image. For example, the feature vector can identify patch size, particle size, particle shape, average pixel intensity, and/or image mean grayscale value. Patch size can be the size of the total image. The image size can be zoomed, as discussed previously. The background can also be expanded, as discussed previously. The patch size is the size of the image prior to any of these changes. The particle size can be the size of the sample cell or reference cell in the image. Optionally, the cell size can appear larger or smaller within the image, as shown, for example in FIG. 9. The particle size of the sample cell in the sample image 905 is smaller than the particle size of the reference cell in the reference image 910. The particle size can appear larger or smaller within the image based on, for example, the magnification used during image capture. The particle shape can be the shape of the sample cell or reference cell in the image. The average pixel intensity can be calculated by selecting multiple pixels from the image, determining an intensity of each of the selected pixels, and calculating the average intensity of the selected pixels. The mean greyscale value of an image can be calculated by selecting multiple pixels from the image, determining a greyscale value for each pixel, and calculating the mean value of the multiple calculated greyscale values. Other features can be identified and utilized for the feature vector for each image.

At 510, computer system 200 can calculate a distance metric for each reference image of the plurality of reference images from the sample image. For example, computer system 200 can utilize the feature vector to calculate a distance metric between each reference image and the sample image. The smaller the distance metric value is, the more similar the reference image is to the sample image. The distance metric value can then be utilized to rank the reference images in order of most to least similar to the sample image.

Optionally, the distance metric can be defined as following:

$$\|\vec{F}_i - \vec{F}_j\| = \sqrt{\sum_{k=0}^{N-1} (f_{i,k} - f_{j,k})^2}$$

In this distance metric definition, the i-th reference image feature vector $\vec{F}_i$ having k-th component of $f_{i,k}$ where $k \in [0, N-1]$ with N as the dimensionality of the feature vector. Candidate features can be based on, for example, image size, particle size in the image, particle shape in the image, average pixel intensity of the image, or particle/patch mean grayscale value. The smaller the distance metric value, the more similar between the i-th (reference) and j-th (sample) image.

FIG. 6 illustrates a flowchart of an example of a process 600 for aligning images. Process 600 can be performed as part of step 330 of FIG. 3. Process 600 can be implemented on, for example the system 100 of FIG. 1 and more specifically as program code on computer system 200 of FIG. 2.

Figure 9:
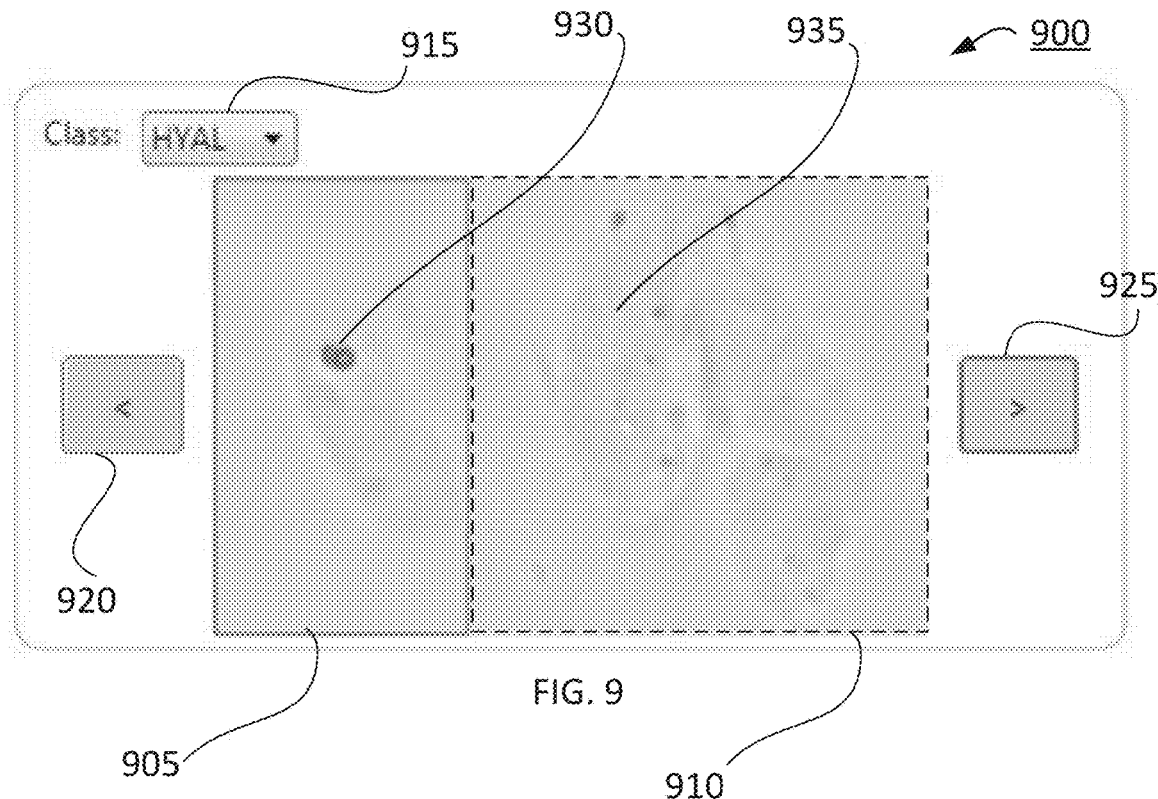
FIGS. 9-14 illustrate examples of images displayed according to embodiments.
Figure 11:
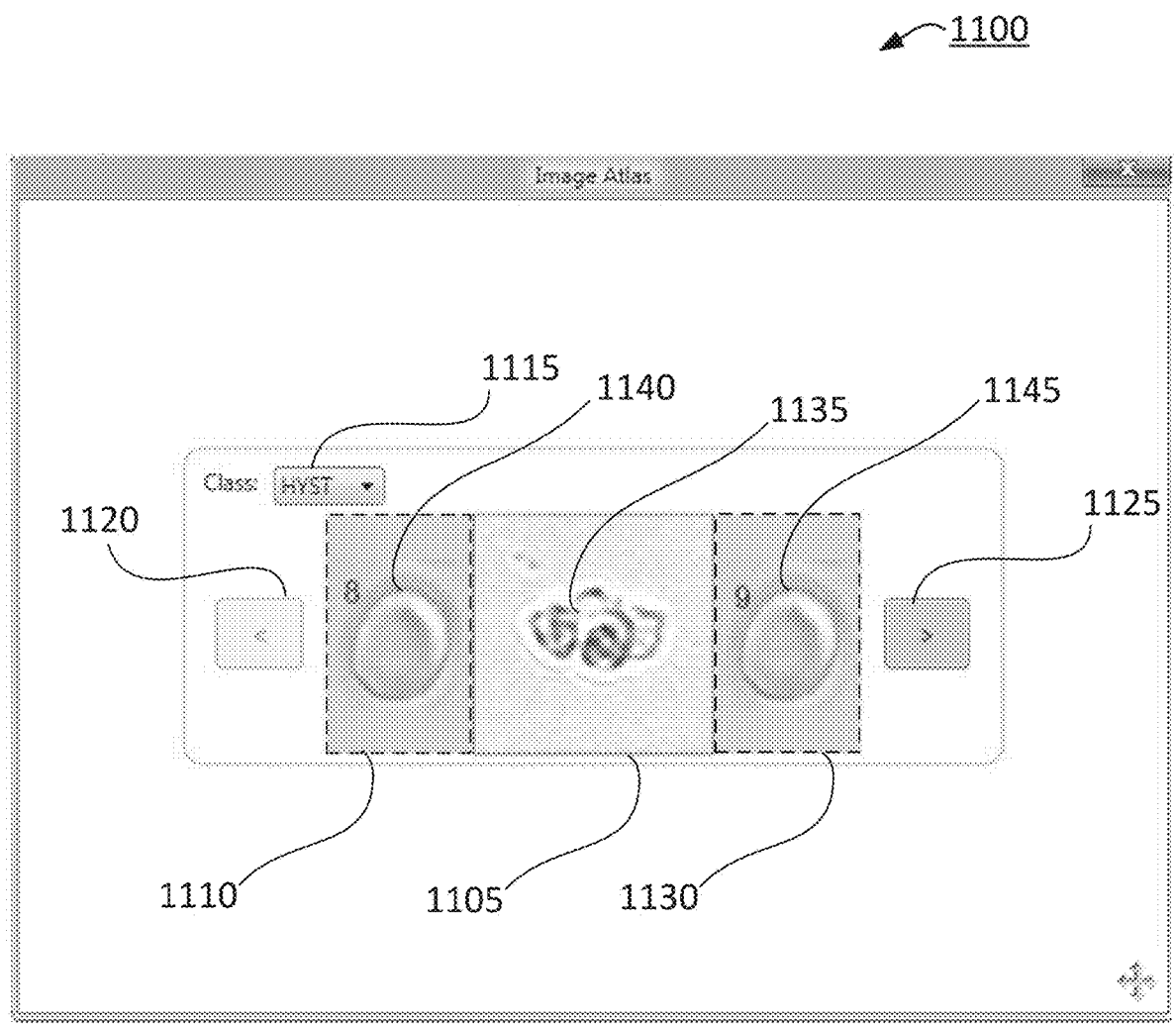
Figure 12:
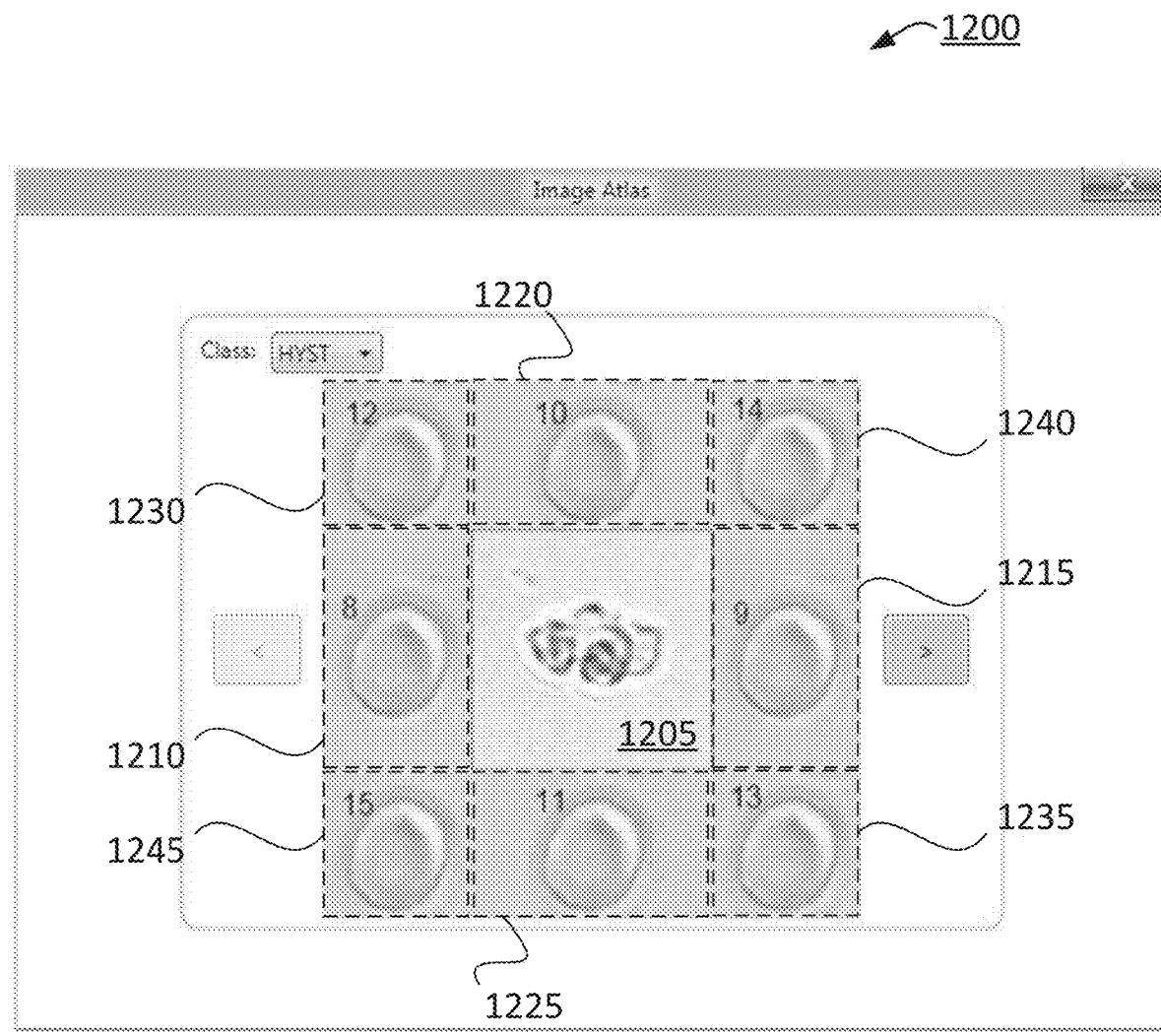

At 605, computer system 200 can determine a first display location for displaying the sample image in the user interface within a first cell of a grid. For example, the images can be displayed in a user interface in a grid such that the sample image is in the center and the reference images are adjacent to the sample image. For example, FIG. 9 shows sample image 905 adjacent to reference image 910. Similarly, as another example, FIG. 11 shows sample image 1105 adjacent to both reference images 1110 and 1115. As yet another example, FIG. 12 shows sample image 1205 adjacent to reference images 1210, 1215, 1220, and 1225. FIG. 12 also shows sample image sharing a corner with reference images 1230, 1235, 1240, and 1245, each of which is adjacent to another reference image. Optionally, the sample image is placed in the center of the grid such that it can be adjacent to as many reference images as possible, as shown in FIG. 12.

At 610, computer system 200 can determine a second display location adjacent to the first display location for displaying the first reference image in the user interface within a second cell of the grid. Examples of the sample image being adjacent to the reference image can be found in FIGS. 9-14. For example, sample image 905 can be adjacent to reference image 910 as shown in FIG. 9.

At 615, computer system 200 can align a centroid of the first reference image within the second display location with a centroid of the sample image within the first display location. For example, the center of the sample image can be determined and placed such that it is located at the center of the first display location, which can be the center of the first cell of the grid (e.g., location of sample image 905 in FIG. 9). The computer system 200 can also determine the center of the first reference image and placed such that it is located at the center of the second display location, which can be the center of the second cell of the grid (e.g., location of reference image 910 in FIG. 9). Because of the definition of a grid, the center of the first display location and the center of the second display location, which are adjacent in the grid, have a common center of the adjacent edges (as shown in FIG. 9). Optionally, other methods can be used such that the centers of the sample image and the first reference image can be aligned by selecting a display location for each that result in the centroids of each image being aligned.

FIG. 7 illustrates a flowchart of an example of a process 700 for dynamically filling the background of an image. Process 700 can be performed as part of step 335 of FIG. 3. Process 700 can be implemented on, for example the system 100 of FIG. 1 and more specifically as program code on computer system 200 of FIG. 2.

At 705, computer system 200 can expand the background of the first reference image within the second cell to fill the second cell. Optionally, the first reference image can have, for example, a smaller height than the sample image. If, for example, the sample image and first reference image adjacent side is a vertical side, the adjacent sides of the first reference image and sample image will be different. Similarly, if, for example, the sample image and first reference image adjacent side is a horizontal side, and the width of the first reference image is smaller than the width of the sample image, the adjacent sides of the images will be different. The background of the first reference image can be expanded to ensure that the adjacent sides of the first reference image and sample image will be the same. Optionally, the size (height and/or width) of the sample image can be smaller than the size of the first reference image. In such embodiments, the sample image background can be expanded.

At 710, computer system 200 can determine a background color of the first reference image. The background color of the first reference image can be determined in a number of ways. For example, a process for determining a mean background color as explained in detail in FIG. 8 can be used to determine the background color. Optionally, selecting a standard color can be used as the background color of the reference image. For example, if all reference images have the same background color, the background color will always be the same and can be already known.

At 715, computer system 200 can fill the expanded background of the first reference image with the background color. For example, the second cell of the grid can be filled with the determined background color such that when displayed in the user interface, the first reference image appears to be expanded without modifying the first reference image itself. Optionally, the first reference image can be processed to expand the image size and fill the expanded pixels with the determined background color.

Figure 8:
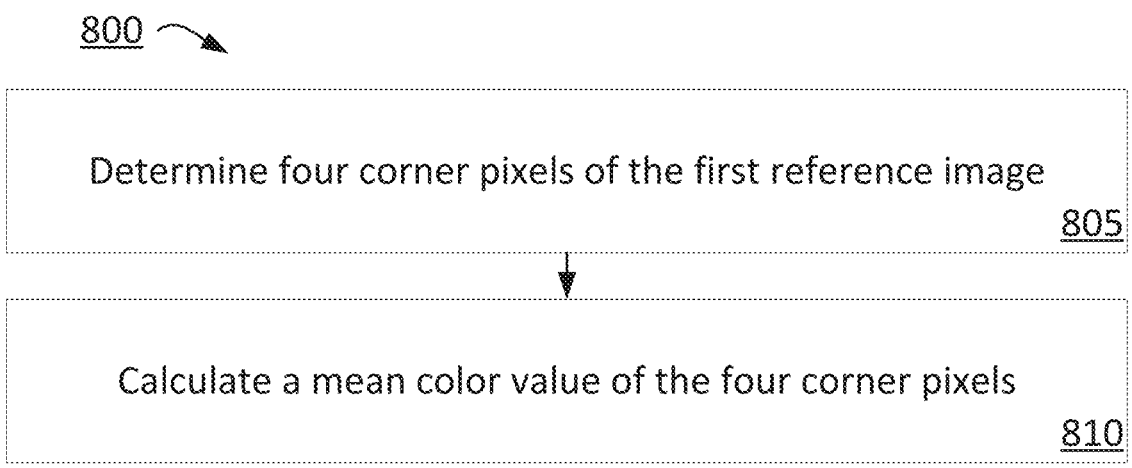
FIG. 8 illustrates a flowchart of an example of a process for determining a background color of an image according to an embodiment.

FIG. 8 illustrates a flowchart of an example of a process 800 for determining a background color of an image. Process 800 can be performed as part of step 710 of FIG. 7. Process 800 can be implemented on, for example the system 100 of FIG. 1 and more specifically as program code on computer system 200 of FIG. 2.

At 805, computer system 200 can determine the four corner pixels of the first reference image. Typical images have 4 corners, and a corner pixel in each corner can be used. For example, if the image patch is of size W×H pixels, the four corner pixels are: [0, 0], [W−1, 0], [0, H−1], [W−1, H−1]. Optionally, more or fewer pixels can be used. Optionally, any number of pixels can be used selected from edge pixels. Optionally, an edge pixel can be any pixel along the edge of the image. Optionally, the edge can be pixels within a threshold distance to the absolute edge of the image, for example, three pixels in distance from the absolute edge of the image.

Figure 13:
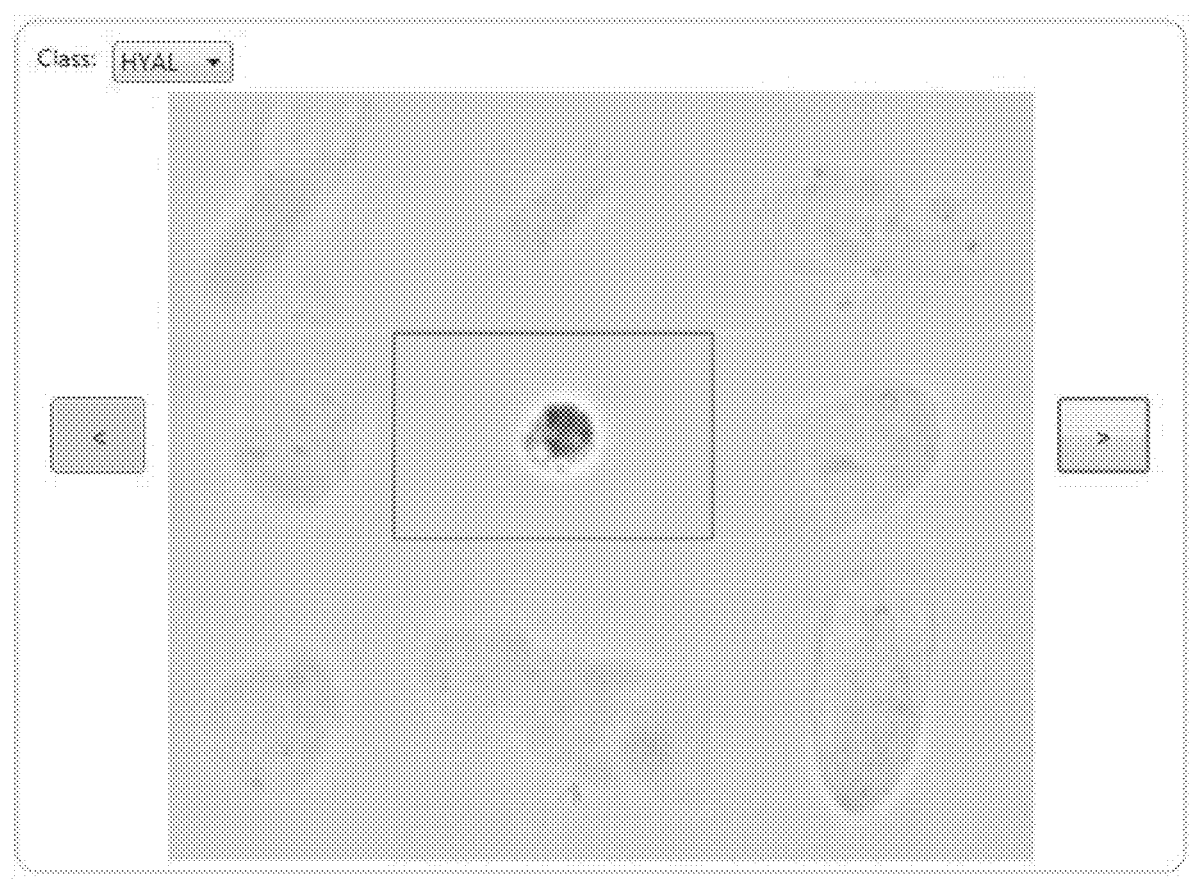
Figure 14:
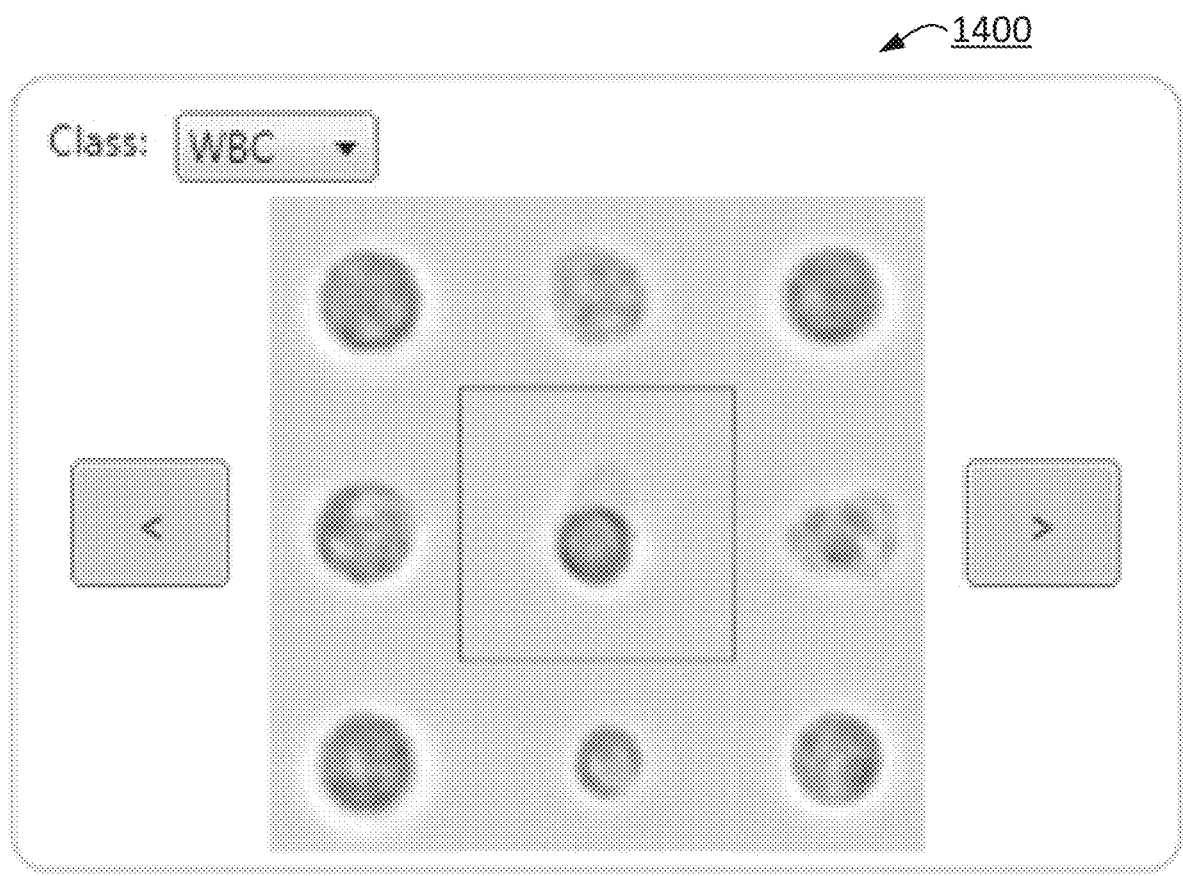

At 810, computer system 200 can calculate a mean color value of the four corner pixels. The mean color value can be determined by first determining a color value of each of the four corner pixels (or each pixel identified for determining the background color if other edge pixels are used, for example). Once the color value for each of the four corner pixels is determined, the computer system 200 can use the color value from each of the four corner pixels to calculate the mean color value of the four corner pixels. The mean can be calculated for each color component, e.g., Red, Green, Blue and Alpha. Optionally, any selected pixels can be used to calculate the mean color value of the background. The mean color value can then be used as the background color of the image. Determining the mean color value can help reduce distractions by filling the reference image background with a color that substantially matches the entire background of the image. Examples of an aligned and dynamically filled grid of a sample image and eight reference images is shown at FIGS. 12-14.

FIGS. 9-14 illustrate examples of images displayed according to embodiments. FIG. 9 displays a portion of a user interface 900 that can be used to compare sample image 905 of sample particle 930 with reference image 910 of reference particle 935. The user interface 900 can include a class indicator 915, a forward navigation button 925, and a backward navigation button 920.

The class indicator 915 can be an indication of an annotation associated with the reference image 910. As shown in FIG. 9, the reference image 910 can have the annotation "HYAL" associated with it. HYAL can mean, for example, that the reference image 910 has been classified as a hyaline cast. The classification annotation or feature tag can be selected by a user, as shown in FIG. 9, using, for example, a drop down selective list. Options included for selection can include, for example, the list provided at Table 1. The list provided at Table 1 includes different cell types or features of cells that can be identified. Once the selection is made by the user for class indicator 915, the selection of the reference images can be made, such as, for example, as explained in detail with respect to step 315 of FIG. 3.

TABLE 1

| Parameter | Name | Group Name |
| --- | --- | --- |
| RBC | RBC | Red blood cell |
| DRBC | DRBC | Red blood cell |
| RBCC | RBCC | Red blood cell |
| WBC | WBC | White blood cell |
| WBCC | WBCC | White blood cell |
| BACT | BACT | Bacteria |
| SQEP | SQEP | Epithelial cell |
| NSE | NSE | Epithelial cell |
| TREP | TREP | Epithelial cell |
| REEP | REEP | Epithelial cell |
| CAOX | CAOX | Crystal |
| URIC | URIC | Crystal |
| TPO4 | TPO4 | Crystal |
| CAPH | CAPH | Crystal |
| CYST | CYST | Crystal |
| TYRO | TYRO | Crystal |
| LEUC | LEUC | Crystal |
| CHOL | CHOL | Crystal |
| AMOR | AMOR | Crystal |
| UNCX | UNCX | Crystal |
| HYAL | HYAL | Cast |
| CELL | CELL | |
| GRAN | GRAN | Cast |
| WAXY | WAXY | Cast |
| UNCC | UNCC | Cast |
| MUCS | MUCS | Mucus |
| SPRM | SPRM | Sperm |
| BYST | BYST | Yeast |
| HYST | HYST | Yeast |
| TRCH | TRCH | Unclassified |
| UNCL | UNCL | Unclassified |

As shown in FIG. 9, there is no gap between the images 905 and 910 shown in user interface 900 to remove the distraction associated with having differing colors between the images. Sample image 905 can be obtained as described with respect to receiving a sample image at step 310 of FIG. 3. Reference image 910 can be selected as described with respect to selecting reference images at step 315 of FIG. 3.

Forward navigation button 925, when selected by a user, can cause the reference image 910 to be replaced with another reference image in the user interface display. Optionally, the forward navigation button 925 can select the next reference image in the ordered list determined by similarity, as described with respect to step 325 of FIG. 3. Optionally, the forward navigation button 925 can select the next reference image selected by the computer system in, for example, random order from the group of reference images that include the annotation or tag indicated by class indicator 915.

Backward navigation button 920, when selected by a user, can cause the reference image 910 to be replaced with another reference image in the user interface display. Optionally, the backward navigation button 920 can select the previous reference image in the ordered list determined by similarity, as described with respect to step 325 of FIG. 3. Optionally, the backward navigation button 920 can select the previously viewed reference image, whether from an ordered list or not.

Figure 10:
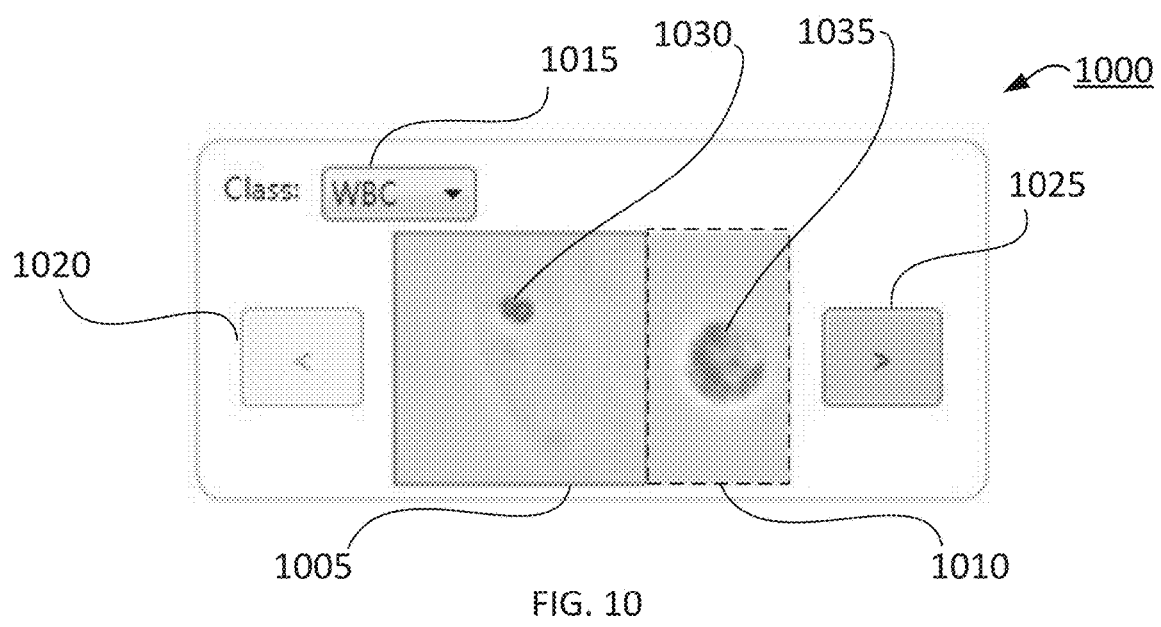

FIG. 10 displays a portion of a user interface 1000 much like the portion of a user interface 900 of FIG. 9. As shown in FIG. 10, the sample image 1005 is the same image as sample image 905 of FIG. 9. The sample image 1005 is an image of sample particle 1030 and the reference image 910 is an image of reference particle 1035. The user interface 1000 also includes a class indicator 1015, a forward navigation button 1025, and a backward navigation button 1020. User interface 1000 can result from the class indicator 915 in FIG. 9 having a new selection identified by the user. For example, if a user is utilizing user interface 900 and selects using class indicator 915 from HYAL as indicated at class indicator 915 of FIG. 9 to WBC as indicated by class indicator 1015 of FIG. 10. WBC can mean white blood cell. The resulting user interface 1000 can then show a reference image 1010 that has a WBC annotation.

The class indicator 1015 can be implemented in the same way as described above with respect to class indicator 915 of FIG. 9. Forward navigation button 1025 can be implemented in the same way as described above with respect to forward navigation button 925 of FIG. 9. Backward navigation button 1020 can be implemented in the same way as described above with respect to backward navigation button 920 of FIG. 9.

As shown in FIGS. 9 and 10, the portion of the user interface 900 is larger than the portion of the user interface 1000. By looking at FIGS. 9 and 10, it can be seen that sample image 905 is the same width as sample image 1005, but the height of sample image 905 is larger than the height of sample image 1005. The sample image 905 and sample image 1005 are both of the same sample cell, and are the same sample image. However, the sample image 905 and sample image 1005 are different sizes (height). This can be because reference image 910 is larger than reference image 1010. In such case, the sample image 905 height could be expanded and dynamically filled as described with respect to steps 330 and 335 of FIG. 3 to ensure the adjacent edge of sample image 905 and reference image 910 are the same size.

FIG. 11 illustrates a portion of a user interface 1100 similar to user interface 900 and user interface 1000. User interface 1100 includes sample image 1105 of sample particle 1135, reference images 1110 and 1130 of reference particles 1140 and 1145 respectively, forward navigation button 1125, backward navigation button 1120, and class indicator 1115. The class indicator 1115 can be implemented in the same way as described above with respect to class indicator 915 of FIG. 9. Forward navigation button 1125 can be implemented in the same way as described above with respect to forward navigation button 925 of FIG. 9. Backward navigation button 1120 can be implemented in the same way as described above with respect to backward navigation button 920 of FIG. 9.

Sample image 1105 can be obtained as described with respect to receiving a sample image at step 310 of FIG. 3. Reference images 1110 and 1130 can be selected as described with respect to selecting reference images at step 315 of FIG. 3. For demonstration purposes only, reference images 1110 and 1130 of reference particles 1140 and 1145 are the same image and are of a test particle. Optionally, for example if the reference database has few reference images, the same reference image can be displayed to the user to enhance the user's ability to identify similarities between the sample image and the reference image. Optionally, the same reference image can be displayed multiple times in the same or different positions of the grid display after selection of the forward or backward navigation buttons 1120 or 1125. The multiple displays can be due to, for example, the number of reference mages in the reference database and a desire to fill every cell of the display grid.

In FIG. 11, it can be seen that two reference images 1110 and 1130 are displayed, each on different adjacent edges of sample image 1105. The selection of the location of the reference image 1110 and reference image 1130 can be based on the similarity of the images, for example. The more similar image can be displayed first, where reference image 1110 is located, and the second most similar image can be displayed second, where reference image 1130 is located.

For image layout modes which involve presenting more than one reference image and mostly in one dimension, e.g., the "3×1" layout (as described in FIG. 19), the reference images can be ordered according to the image's similarity metrics in the direction of the X axis. The following diagram illustrates the point:

Similarly for image layout mode of "3×3," which involves two dimensions, the reference images can be ordered based on the spiral coordinate as defined by image neighborhood. The following diagram illustrates that the ordering ([0], [1], . . . , [7]) of reference images to match with the natural image neighborhood ordering:

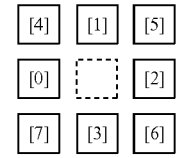

When the number of reference images is not divisible by the sliding window size (Sliding window size for image layout of m×n is m*n−1. For example, the image layout mode of "3×3" has a sliding window size of 3*3−1=8), the selection is adjusted so there are no empty grid cells when displaying reference images. There can be, for example, no difference in selection regardless of the navigation direction (e.g., moving forward or backward in the list of reference images using the forward or backward navigation buttons, as described with respect to FIG. 9). For example, if there are nine (9) reference images for an image layout mode of "3×3," i.e., sliding window size of 8, there are two sliding windows possible for display, with the first window using the first 8 reference images, and the last window using the last 8 reference images. Specifically, for a list of N reference images, for image layout of m×n, the count of sliding windows is given by:

$$K = \begin{cases} N/(m*n-1), & \text{where } N \bmod (m*n-1) = 0 \\ N/(m*n-1)+1, & \text{where } N \bmod (m*n-1) \neq 0 \end{cases},$$

where m≠1 or n #1 and mod denotes the mathematical modulo operation. And the i-th sliding window starting index (into the list of N reference images) is given by:

$$W_i = \begin{cases} i*(m*n-1), & \text{where } i \neq K-1 \\ N-(m*n-1), & \text{where } i = K-1 \end{cases},$$

where m≠1 or n≠1,$^{i \in [0 \ K-1]}$

FIG. 12 illustrates a portion of a user interface 1200 similar to the user interfaces in FIGS. 9-11. User interface 1200 displays eight reference images 1210, 1215, 1220, 1225, 1230, 1235, 1240, and 1245. FIG. 12 also includes a forward navigation button, backward navigation button, and class indicator.

FIG. 13 illustrates a portion of a user interface 1300 similar to the user interfaces in FIGS. 9-12. User interface 1300 displays eight reference images (not numbered). FIG. 13 also includes a forward navigation button, backward navigation button, and class indicator. User interface 1300 is an example of a user interface that a user could use for comparison of a sample image, which is within the box in the center of the image, with eight reference images, the reference images surrounding the sample image.

FIG. 14 illustrates a portion of a user interface 1400 similar to the user interfaces in FIGS. 9-13. User interface 1400 displays eight reference images (not numbered). FIG. 14 also includes a forward navigation button, backward navigation button, and class indicator. User interface 1400 is an example of a user interface that a user could use for comparison of a sample image, which is within the box in the center of FIG. 14, with eight reference images, the reference images surrounding the sample image.

Figure 15:
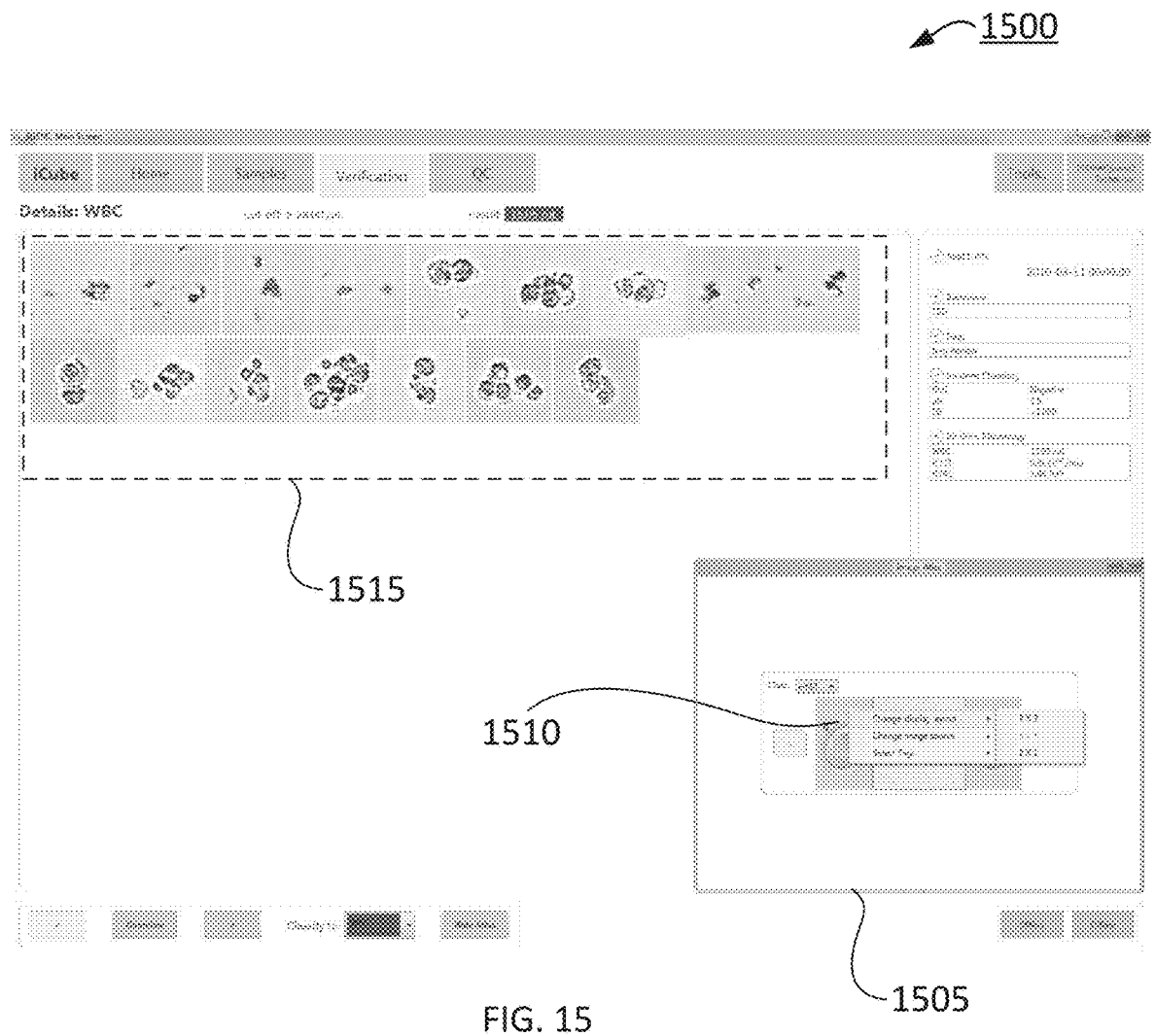
FIGS. 15-21 illustrate examples of a user interface according to embodiments.

FIGS. 15-18 illustrate additional examples of user interfaces. FIG. 15 illustrates a user interface 1500, which includes a floating window 1505 that can be, for example, the portion of user interface 1900 as shown in FIG. 19. Floating window 1505 can include a context menu 1510 that can be displayed when a user right-clicks within floating window 1505. The sample image displayed in floating window 1505 (behind the context menu 1510) can be selected, for example, by a user selecting one of the images from the image selection section 1515. Optional selections that can be available in the context menu can include, for example, changing the display layout, changing the reference image source, selection of one or more tags, changing the orientation of one or more images, and zooming in or out of one or more images.

Figure 16:
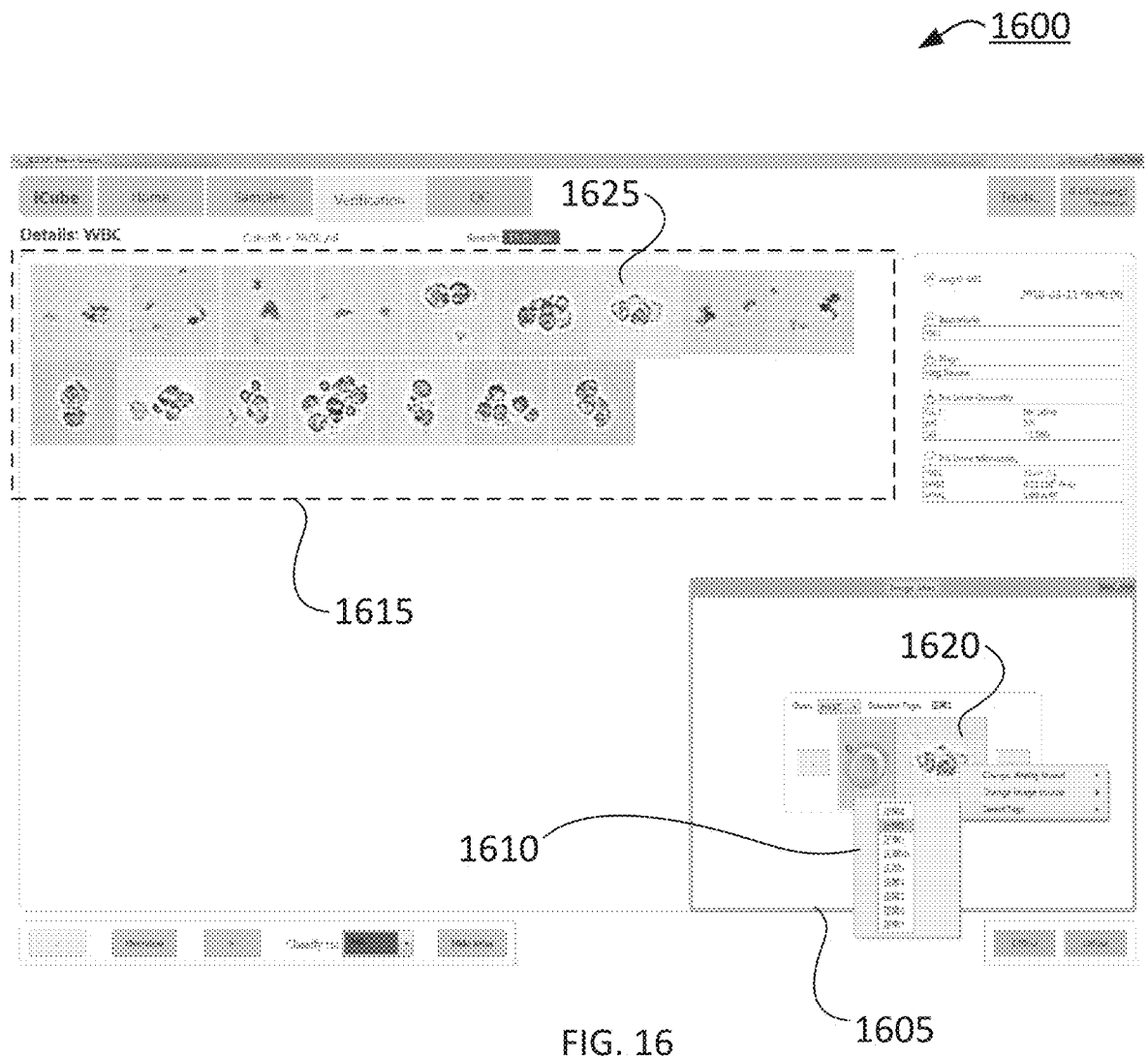
Figure 20:
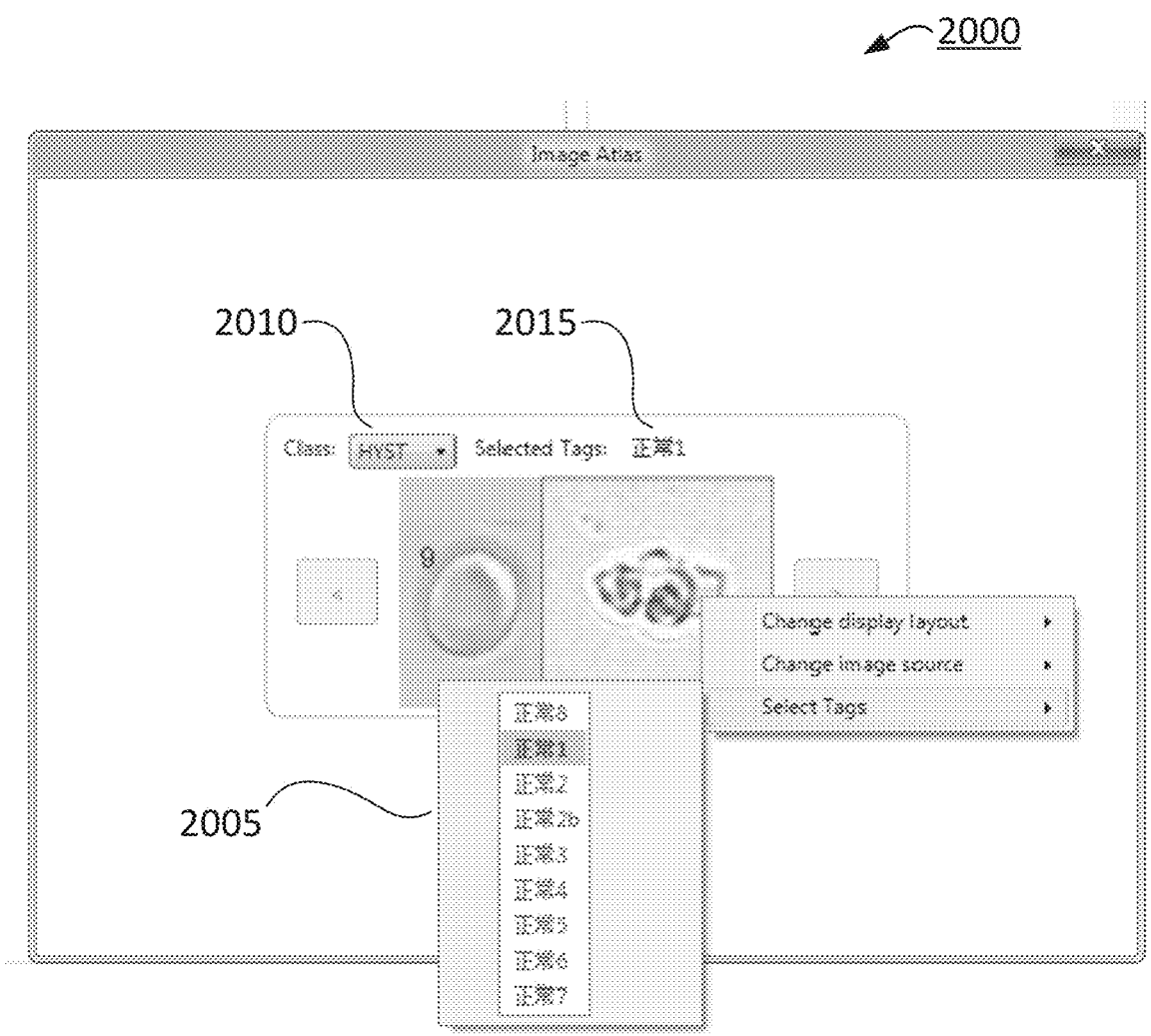

FIG. 16 illustrates a user interface 1600, which includes a floating window 1605 that can be, for example, the portion of user interface 2000 as shown in FIG. 20. Floating window 1605 can include a context menu 1610 that can be displayed when a user right-clicks within floating window 1605. The sample image 1620 displayed in floating window 1605 can be selected, for example, by a user selecting one of the images from the image selection section 1615. In this case, the sample image 1620 was selected by the user selecting image 1625 from the image selection section 1615.

Figure 17:
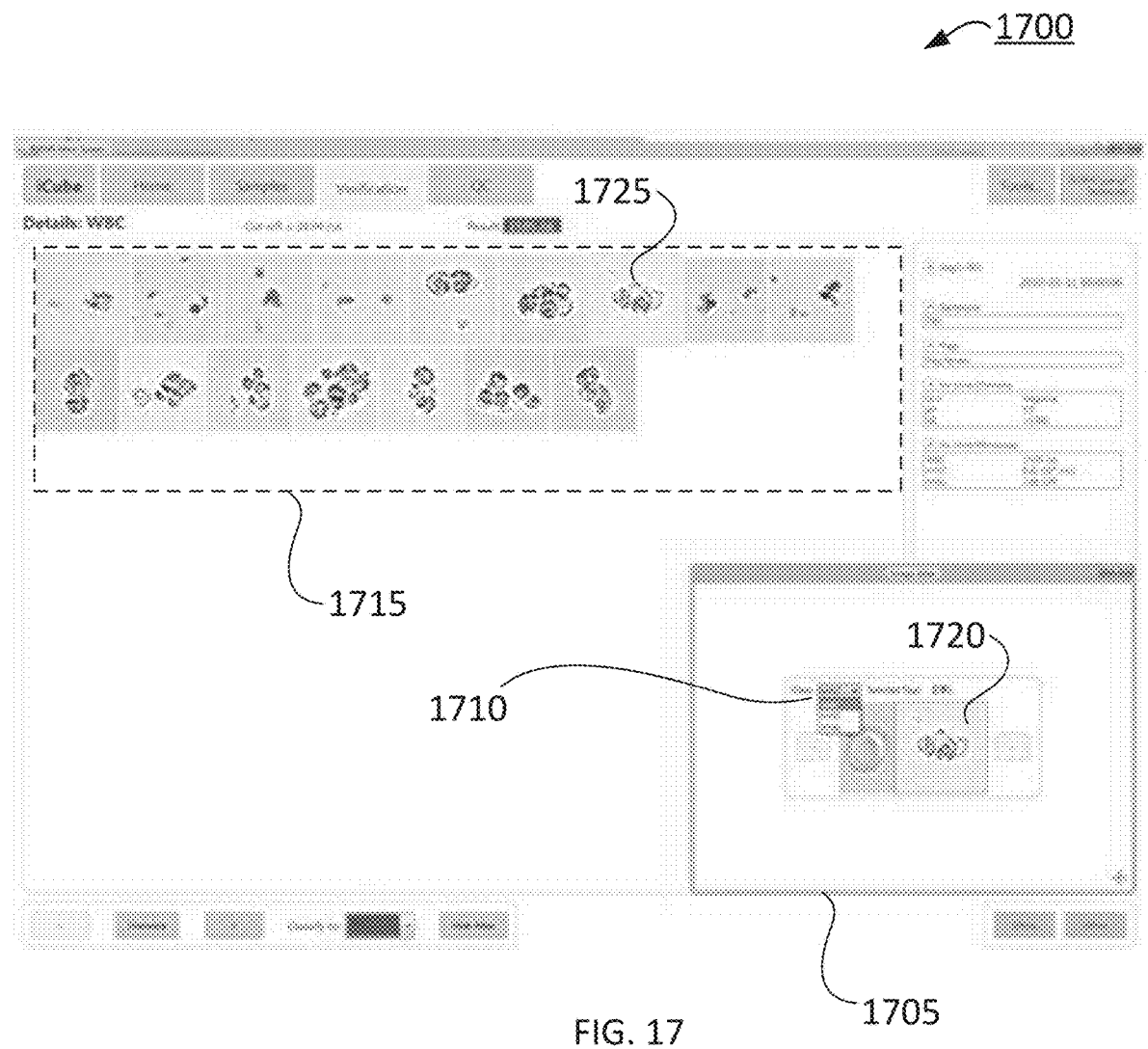
Figure 21:
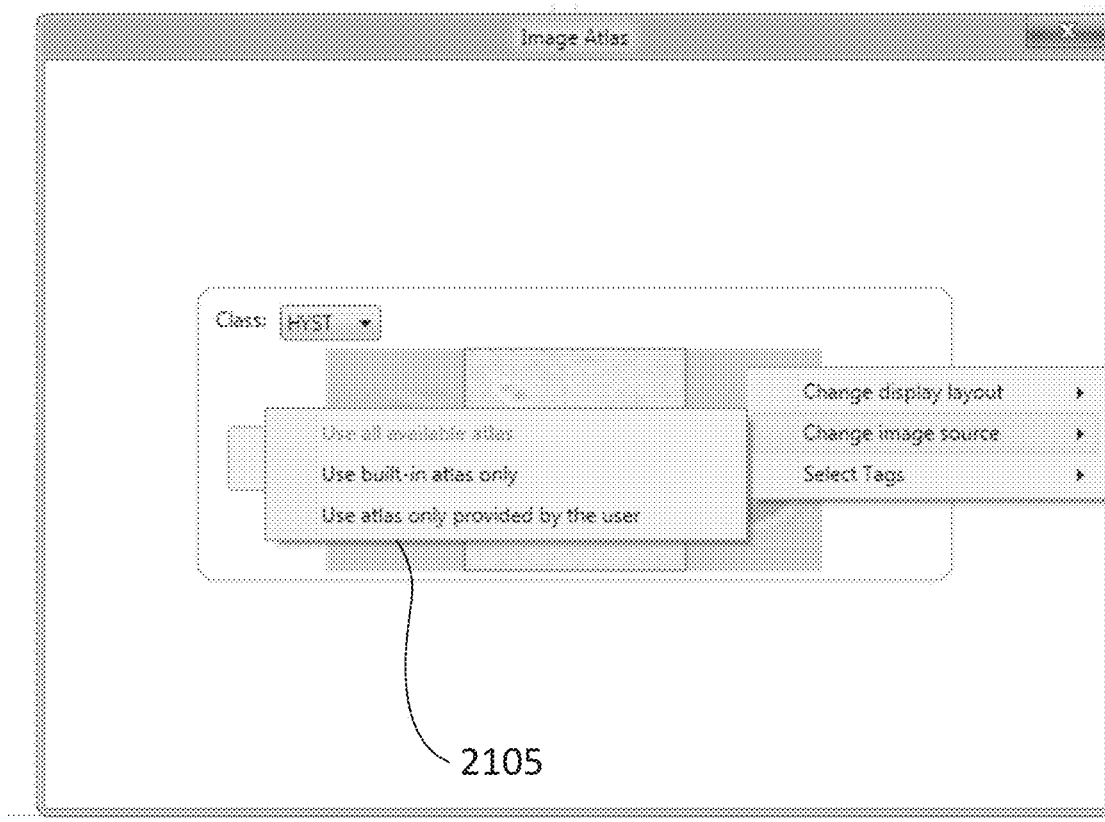

FIG. 17 illustrates a user interface 1700, which includes a floating window 1705 that can be, for example, the portion of user interface 2100 as shown in FIG. 21. Floating window 1705 can include a class identifier 1710 that can allow the user to select a tag or annotation for selection of reference images, as described with respect to step 325 of FIG. 3. The sample image 1720 displayed in floating window 1705 can be selected, for example, by a user selecting one of the images from the image selection section 1715. In this case, the sample image 1720 was selected by the user selecting image 1725 from the image selection section 1715.

Figure 18:
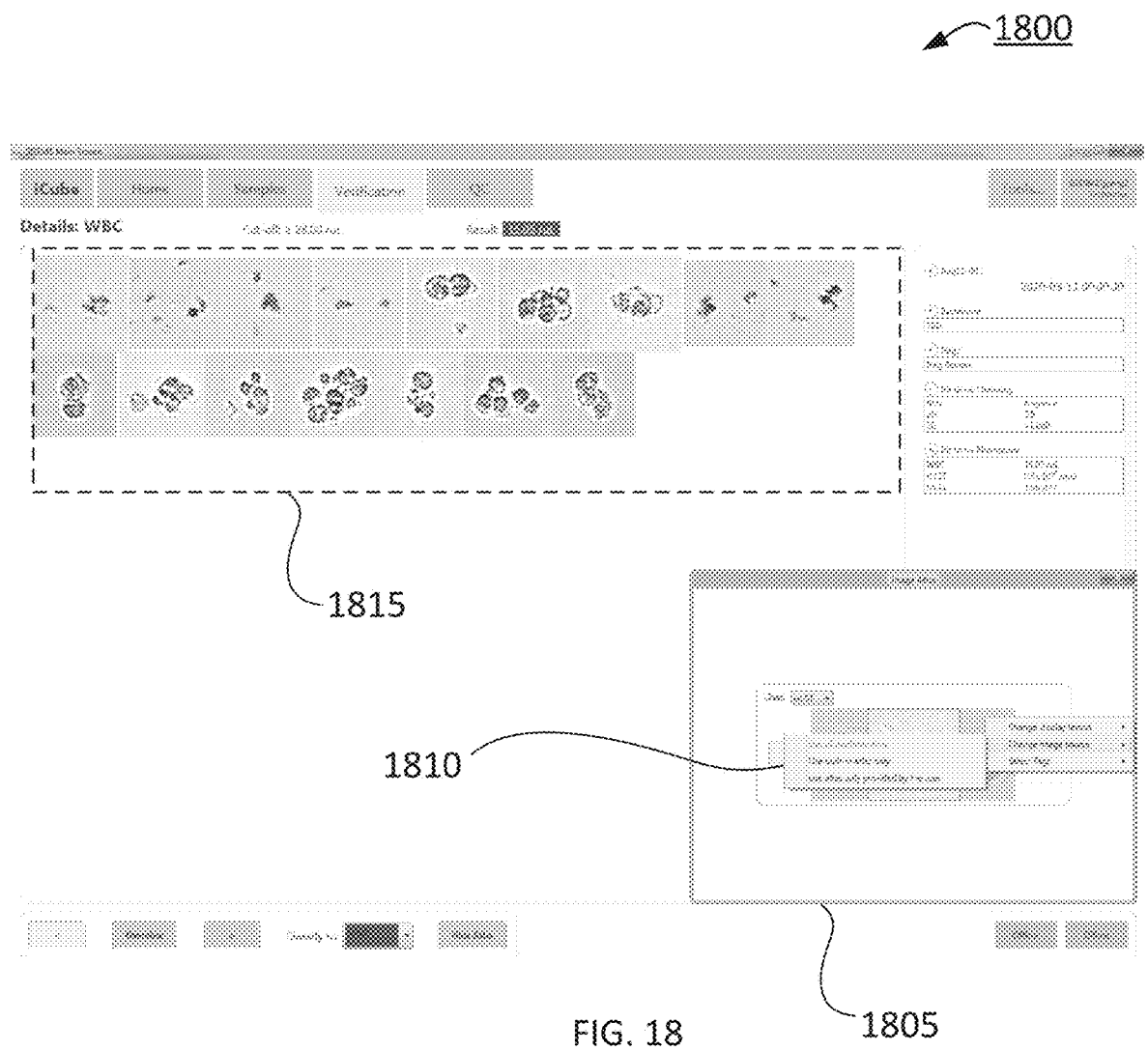
Figure 19:
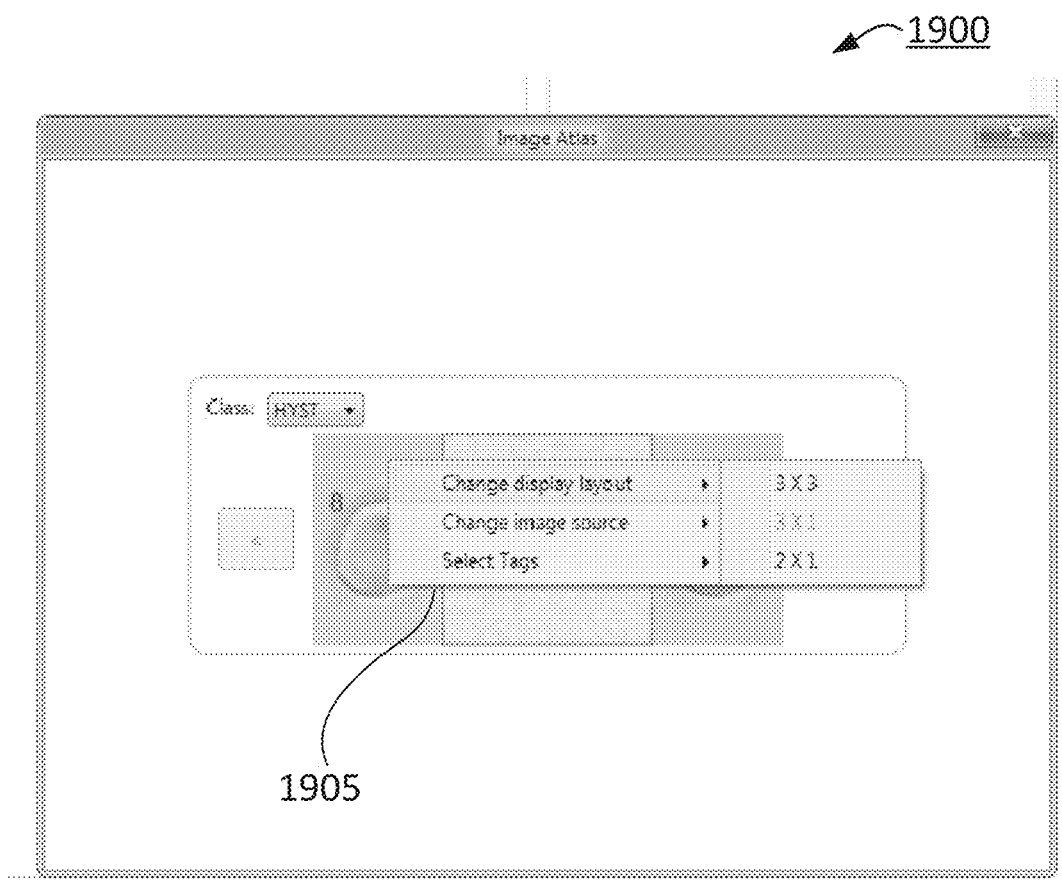

FIG. 18 illustrates a user interface 1800, which includes a floating window 1805 that can be, for example, the portion of user interface 2100 as shown in FIG. 21. Floating window 1805 can include a context menu 1810 that can be displayed when a user right-clicks within floating window 1805.

FIG. 19 illustrates a portion of a user interface 1900, which can be the portion of the user interface depicted as floating window 1505 as shown in FIG. 15. Context menu 1905 can be displayed when a user right clicks in the portion of the user interface 1900. The context menu 1905 can change the display layout of the sample image and reference images. The "3×1" selection is greyed out because the display is already set to a 3×1 grid. The 3×1 option is shown, for example, in FIG. 11. Another optional selection can include "2×1," which is shown, for example, in FIGS. 9 and 10. Another optional selection can include "3×3," which is shown, for example, in FIGS. 12-14.

FIG. 20 illustrates a portion of a user interface 2000, which can be the portion of the user interface depicted as floating window 1605 as shown in FIG. 16. Context menu 2005 can be displayed when a user right clicks in the portion of the user interface 2000. The context menu 2005 can allow the user to "select tags," which can be a selection of a tag for identifying the reference images for selection within the reference image database and can further narrow the displayed images to not only the selected class but also by selected tags. In this way, the user can customize a multi-selection of class and tags for filtering. In FIG. 20 it can be seen that optionally, a user can select a classification of the reference images to select from, which is shown by the class selection box 2010. In this case the selected class is "HYST." Additionally, tags can be selected to further narrow the selection based on other features of the particles that have been tagged on the reference images in the reference database. The context menu 2005 can allow the user to select one or more tags for filtering the displayed reference images. The selected tag is shown at 2015. The displayed reference images can be selected from the reference image database based on whether the reference image is classified within the selected class and has the selected tags associated with the reference image as well.

FIG. 21 illustrates a portion of a user interface 2100, which can be the portion of the user interface depicted as floating window 1805 as shown in FIG. 18. Context menu 2105 can be displayed when a user right clicks in the portion of the user interface 2100. The context menu 2105 can allow the user to change the image source. Selection of the image source can select the database from which the reference images are selected. Options for selection of the image source can be to use a built in source, for example, or use a user selected reference image database, for example. A user selected reference image database can be generated, for example, as described above.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

It is to be understood that the figures and descriptions of embodiments of the invention have been simplified to illustrate elements that are relevant for a clear understanding of the invention. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

All patents, patent publications, patent applications, journal articles, books, technical references, and the like discussed in the instant disclosure are incorporated herein by reference in their entirety for all purposes.

The invention claimed is:

1. A method, comprising:
   receiving, at a computer system, a sample visual image of a sample particle from a biological sample;
   selecting, by the computer system, a plurality of reference images from a database of reference images, each reference image of the plurality of reference images being a reference image of a reference particle from a plurality of reference particles from one or more biological samples;
   determining, by the computer system, an order of the plurality of reference images based on a similarity of each reference image to the sample image;
   selecting, by the computer system, a first reference image from the plurality of reference images based on the determined order;
   physically aligning, by the computer system, the first reference image with the sample image;
   dynamically filling, by the computer system, a physical background image of the aligned first reference image; and
   displaying, by the computer system, the sample image and the dynamically filled and aligned first reference image in a user interface;
   wherein the determining the order of the plurality of reference images comprises:
   comparing, by the computer system, the sample image with each reference image of the plurality of reference images; and
   determining, by the computer system, the similarity of each reference image to the sample image;
   wherein the comparing the sample image with each reference image of the plurality of reference images comprises:
   generating, by the computer system, a feature vector for each of the reference images of the plurality of reference images and the sample image; and
   calculating, by the computer system, a distance metric for each reference image of the plurality of reference images by comparing the feature vectors of each of the plurality of reference images with the feature vectors of the sample image.

2. The method of claim 1, wherein features used to generate the feature vector for each of the reference images of the plurality of reference images and the sample image include at least one of a patch size, a particle size, a particle shape, average pixel intensity, and an image mean grayscale value.

3. The method of claim 1, wherein aligning the first reference image with the sample image comprises:
   determining, by the computer system, a first display location for displaying the sample image in the user interface, the first display location being within a first cell of a grid of cells;

determining, by the computer system, a second display location adjacent to the first display location for displaying the first reference image in the user interface, the second display location being within a second cell of the grid of cells; and aligning, by the computer system, a centroid of the first reference image within the second display location with a centroid of the sample image within the first display location.

4. The method of claim 3, wherein dynamically filling the background of the aligned first reference image comprises:

expanding, by the computer system, the background of the first reference image within the second cell to fill the second cell;

determining, by the computer system, a background color of the first reference image; and filling, by the computer system, the expanded background of the first reference image with the background color.

5. The method of claim 4, wherein determining the background color of the first reference image comprises:

determining, by the computer system, four corner pixels of the first reference image; and calculating, by the computer system, a mean color value of the four corner pixels.

6. The method of claim 1, wherein the plurality of reference images are selected based on a tag associated with each reference image of the plurality of reference images.

\* \* \* \* \*